(12) United States Patent
Carabajal

(10) Patent No.: US 11,324,515 B2
(45) Date of Patent: May 10, 2022

(54) WEARABLE BLOOD FLOW OCCLUSION DEVICE

(71) Applicant: Johnny Xavier Carabajal, Huntington Beach, CA (US)

(72) Inventor: Johnny Xavier Carabajal, Huntington Beach, CA (US)

(*) Notice: Subject to any disclaimer, the term of this patent is extended or adjusted under 35 U.S.C. 154(b) by 0 days.

(21) Appl. No.: 16/380,935

(22) Filed: Apr. 10, 2019

(65) Prior Publication Data

US 2019/0307465 A1 Oct. 10, 2019

Related U.S. Application Data

(60) Provisional application No. 62/655,574, filed on Apr. 10, 2018.

(51) Int. Cl.
*A61B 17/132* (2006.01)
*A61B 17/12* (2006.01)
*A61B 17/00* (2006.01)
*A44B 11/06* (2006.01)

(52) U.S. Cl.
CPC ......... *A61B 17/1322* (2013.01); *A44B 11/065* (2013.01); *A61B 2017/00398* (2013.01); *A61B 2017/12004* (2013.01)

(58) Field of Classification Search
CPC ...... A61B 17/1322; A61B 2017/00398; A61B 2017/12004; A61B 2017/081; A61B 2017/1103; A61B 17/132; A61B 17/1325; A61B 17/1327; A61B 17/135; A44B 11/065
See application file for complete search history.

(56) References Cited

U.S. PATENT DOCUMENTS

| | | |
|---|---|---|
| D679,019 S | 3/2013 | Siddle et al. |
| 2015/0051638 A1* | 2/2015 | Dickinson .......... A61B 17/1322 606/203 |
| 2016/0058130 A1 | 3/2016 | Boney et al. |
| 2016/0332010 A1* | 11/2016 | Lowell ............... A62B 35/0018 |
| 2018/0271541 A1 | 9/2018 | Figueiredo et al. |

* cited by examiner

*Primary Examiner* — Wade Miles
(74) *Attorney, Agent, or Firm* — Total Awareness Consulting Services; Robert Winslow

(57) ABSTRACT

A wearable device comprises a tourniquet configured to occlude blood flow in an artery of a wearer. The tourniquet comprises at least one base plate; two anchor points connected to one of the at least one base plate and configured to anchor a first end of one of two laces; a tunnel strap comprising two lace guides connected to a first end of the tunnel strap, each configured to guide one of the two laces; and a tightening mechanism connected to one of the at least one base plate and comprising a spool configured to accept a second end of each of the two laces, and a knob configured for manually winding a portion of at least one of the two laces onto the spool. The wearable device comprises a wearable item quick release connector connected to the tourniquet, and configured to removably connect to a wearable item.

20 Claims, 25 Drawing Sheets

WEARABLE BLOOD FLOW OCCLUSION DEVICE

CROSS-REFERENCE TO RELATED APPLICATIONS

This application claims the benefit of U.S. Provisional Application No. 62/655,574, filed Apr. 10, 2018, which is hereby incorporated by reference in its entirety.

BACKGROUND

Hemorrhage is the leading cause of combat deaths. In many cases, applying a tourniquet after sustaining a wound in an appendage is too painful to apply effectively. In some cases, a person, such as an injured soldier, law enforcement officer, or government agent loses consciousness and is unable to apply self-aid. Self-aid on multiple extremities is unlikely in most battleground cases since each solder is typically issued one tourniquet. In many cases, medical personnel cannot reach a wounded soldier, law enforcement officer, or government agent in time to locate a tourniquet, place the tourniquet in position, secure the tourniquet on a limb, tighten the tourniquet, and (optionally) lock the tourniquet in a tightened position to cease a hemorrhage.

Many existing tourniquets may not be considered as effective devices to occlude blood flow to prevent spread of venom throughout the body. This is due to the amount of time it typically takes to don and effectively activate many of the existing tourniquets. Venom may be secreted by invertebrates, fish, amphibians, and reptiles. Examples of animals that may secrete venom include stonefish, stingrays, jellyfish, bees, wasps, spiders, komodo dragons, snakes, and scorpions.

Many existing tourniquets may have excess weight and/or bulk. Excess weight and/or bulk may reduce the number of tourniquets carried by a user or a first responder.

Many existing tourniquets may be difficult to place on a limb for effective occlusion. Many existing tourniquets may be difficult to operate. Many existing tourniquets may not be adaptable to a variety of limb sizes and limb types (e.g. legs, arms). Operation by a person who has not been trained in proper tourniquet placement and operation is often too difficult to complete effectively. In some cases, a person may be in too much pain to effectively apply self-aid to occlude blood flow. Operation by medical personnel may take too much time in cases involving mass injuries such as, for example, on a battlefield, in a terrorist attack, in a natural disaster, or after a multivehicle accident.

Many existing tourniquets may not provide the durability and/or the wearability necessary for effective combat and/or immediate use. Many existing tourniquets may be difficult to operate while wearing gloves. Many existing tourniquets may not apply enough pressure to completely occlude blood flow in an artery of a wearer. Many existing tourniquets may rely on a pressure ridge that needs to be located directly over an artery to occlude blood flow. Many existing tourniquets may cause scrunching of tourniquet material during use which may cause unnecessary discomfort to the user and/or may prevent effective occlusion. Many existing tourniquets may locate an adjustment mechanism on a medial side of a limb. In this location, the adjustment mechanism may be engaged or disengaged prematurely.

DETAILED DESCRIPTION OF EMBODIMENTS

Figure 1:
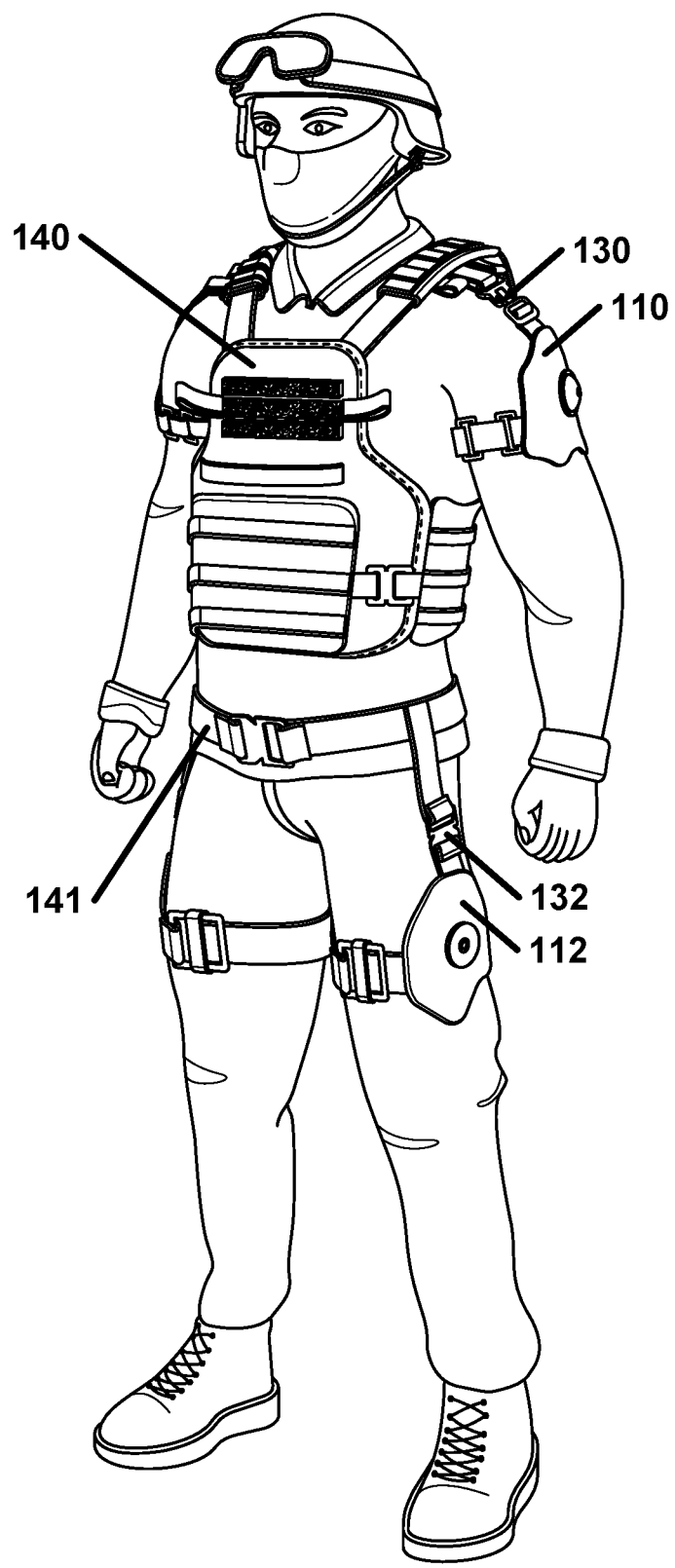
FIGS. 1, 2, and 3 illustrate example wearable devices attached to example wearable items according to various aspects of various embodiments.

Embodiments are configured to cause occlusion of blood flow.

Embodiments may comprise at least one wearable device. A wearable device may be configured for rapid deployment. The wearable device may comprise a tourniquet. The wearable device may be configured such that the tourniquet is located over an artery of a wearer for effective occlusion of blood flow if necessary. The wearable device may be configured for ease of use. The wearable device may be configured for ease of use by a novice.

Embodiments may comprise a tourniquet. The tourniquet may comprise two laces. The two laces may be employed to provide redundancy. The tourniquet may be structurally configured to operate upon the event one of the two laces becomes damaged or cut.

Embodiments may comprise a tourniquet. The tourniquet may comprise a plurality of base plates. The plurality of base plates may be interconnected through employment of at least one hinge. The tourniquet may be foldable. A foldable tourniquet may be more compact and easier to store and/or carry in a folded position.

Embodiments may comprise a tourniquet. The tourniquet may be configured for rapid deployment. The tourniquet may be configured for ease of use. The tourniquet may be configured for ease of use by a novice. A plurality of tourniquets may be stored in a first response vehicle. A plurality of tourniquets may be stored in locations where mass casualty incidents could occur such as but not limited to hospitals, airports, train stations, churches, schools, stadiums, concert venues, combinations thereof, and/or the like.

Embodiments may comprise at least one strap. The at least one strap may comprise at least one organic material.

According to an embodiment, a wearable device may comprise a tourniquet structurally configured to occlude blood flow in an artery of a wearer. The tourniquet may comprise at least one base plate. The tourniquet may comprise two anchor points. Each of the two anchor points may be structurally configured to anchor a first end of one of two laces to one of the at least one base plate. The tourniquet may comprise a tunnel strap comprising two lace guides. The two lace guides may be connected to a first end of the tunnel strap. Each of the two lace guides may be structurally configured to guide one of the two laces. The tourniquet may comprise a tightening mechanism. The tightening mechanism may be connected to one of the at least one base plate. The tightening mechanism may comprise a spool structurally configured to accept a second end of each of the two laces. The tightening mechanism may comprise a knob structurally configured for manually winding a portion of the two laces onto the spool.

According to an embodiment, a wearable device may comprise a wearable item strap. The wearable item strap may be connected to one of at least one base plate. The wearable item strap may be connected to the one of at least one base plate through employment of a single pivot. The wearable item strap may comprise a wearable item quick release connector. Alternatively, the wearable item quick release connector may be connected directly to the one of at least one base plate. The wearable item quick release connector may be connected directly to the one of at least one base plate through employment of a single pivot. The wearable item quick release connector may be structurally configured to removably connect to a wearable item. The wearable item quick release connector may be magnetic. The wearable item may comprise a ballistic plate carrier, a backpack, a belt, a harness, combinations thereof, and/or the like.

According to an embodiment, wearable devices may be connected to wearable items such that tourniquets are automatically located at proximal points of extremities. This automatic location may eliminate the need to don the tourniquet after an injury is sustained.

According to an embodiment, a wearable device may comprise an outer cuff. The outer cuff may be structurally configured to cover at least a portion of a tourniquet. The portion of the tourniquet may comprise two laces. The portion of the tourniquet may comprise two lace guides. The portion of the tourniquet may comprise a first end of a tunnel strap. The portion of the tourniquet may comprise two anchor points. The outer cuff may comprise at least one organic material. The outer cuff may comprise printed instructions for use of the wearable device and/or tourniquet.

According to an embodiment, a tourniquet may comprise a fixed strap. The fixed strap may be connected to one of at least one base plate of the tourniquet. The fixed strap may be connected to the one of at least one base plate through employment of a single pivot. The single pivot may, for example, comprise a single rivet or a single fastener. The fixed strap may be structurally configured to connect to a tunnel strap. The fixed strap may be adjustable. The connection between the tunnel strap and the fixed strap may be adjustable. The tunnel strap may be connected to the fixed strap through employment of a tunnel strap quick release connector. The tunnel strap quick release connector may be adjustable. The tunnel strap quick release connector may be magnetic.

According to an embodiment, a wearable item quick release connector may be structurally configured to removably connect a tourniquet to a wearable item. The wearable item quick release connector may be structurally configured to be adjustable to properly place a tourniquet on an extremity of a user. The wearable item quick release connector may enable the tourniquet to remain in place while the wearable item is adjusted or removed from the wearer.

According to an embodiment, a tourniquet may be structurally configured to enable a user to apply a mechanical advantage to apply sufficient pressure to occlude blood flow. The tourniquet may be structurally configured to apply circumferential pressure to occlude blood flow.

Figure 2:
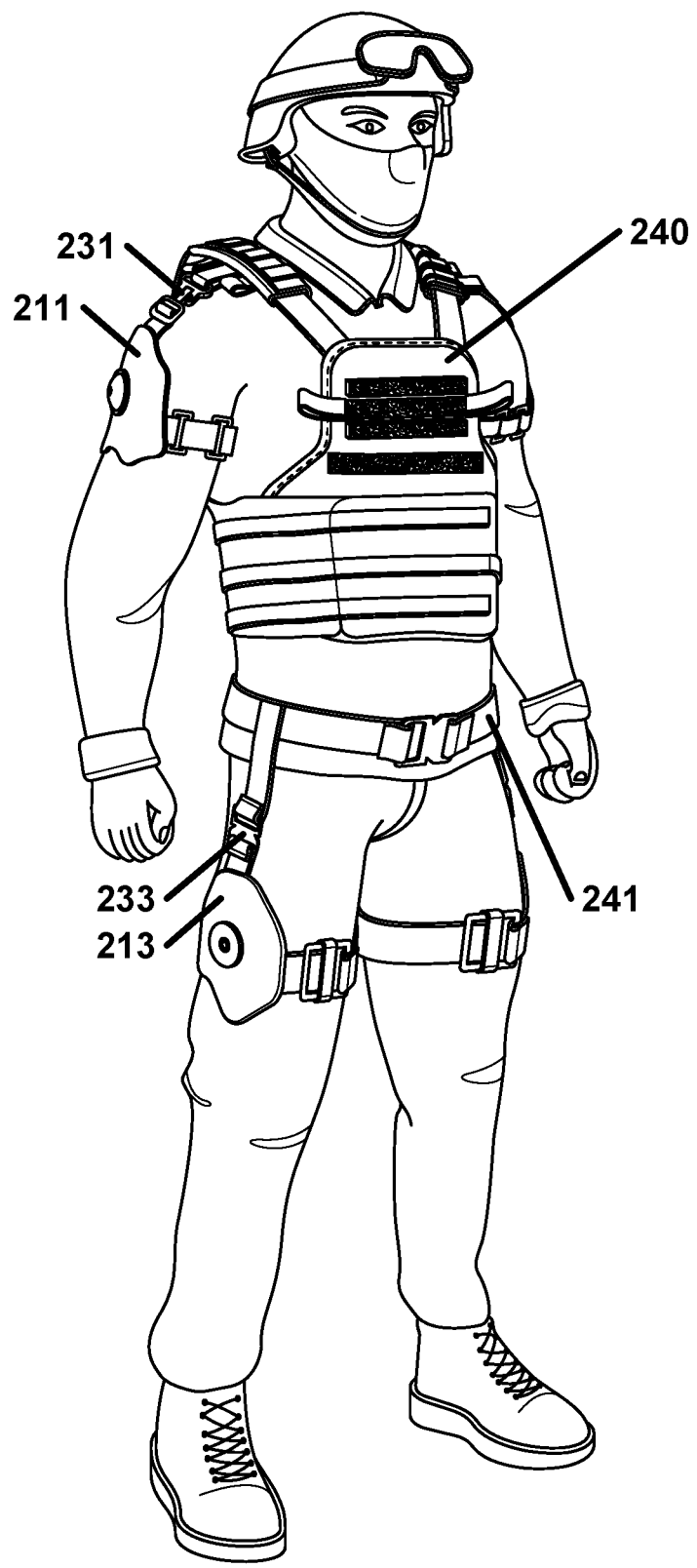
Figure 3:
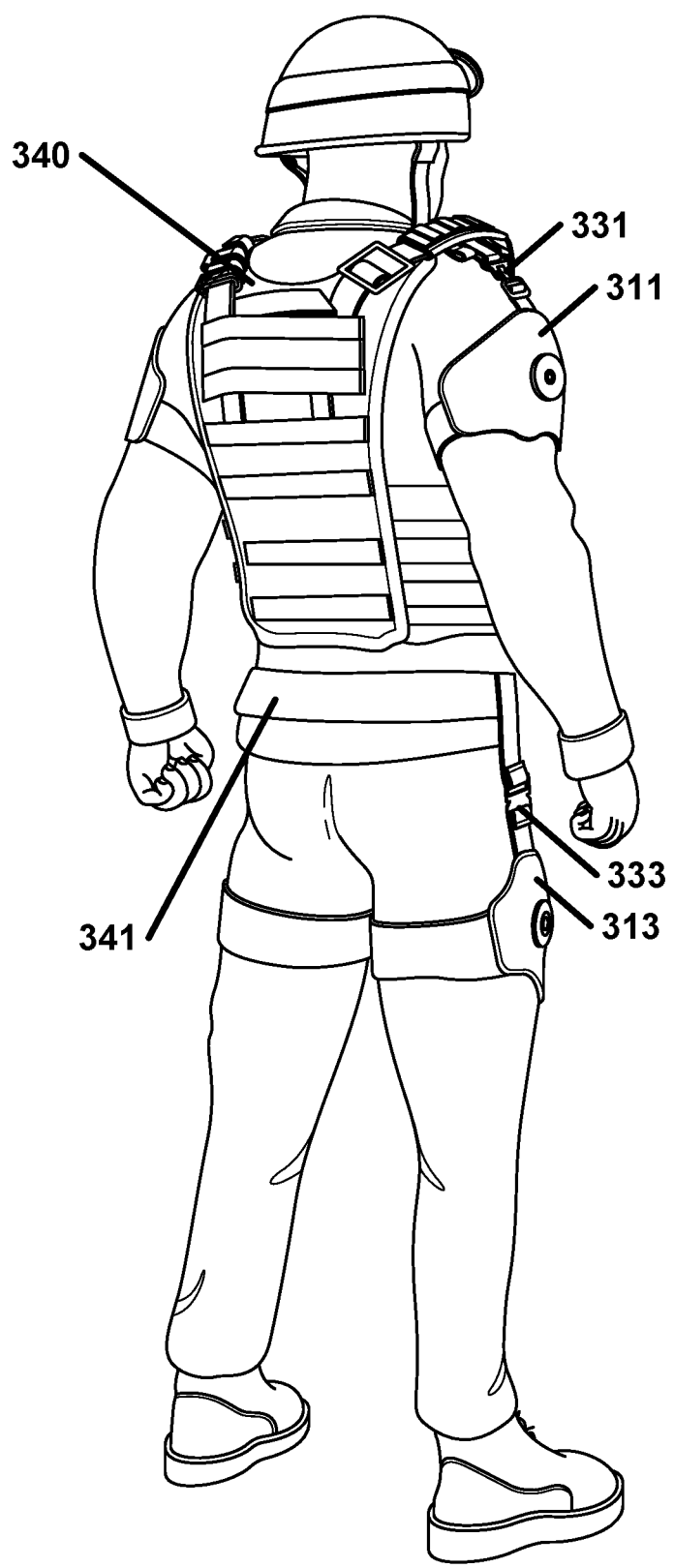

FIGS. 1, 2, and 3 illustrate example wearable devices (110, 112, 211, 213, 311, and 313) attached to example wearable items (140, 141, 240, 241, 340, and 341) according to various aspects of various embodiments. Some of the wearable devices (110, 211, and 311) may be attached to wearable items such as body armor (140, 240, and 340) through employment of wearable item quick release connectors (130, 231, and 331). Some of the wearable devices (112, 213, and 313) may be attached to wearable items such as belts (141, 241, and 341) through employment of wearable item quick release connectors (132, 233, and 333).

Figure 4:
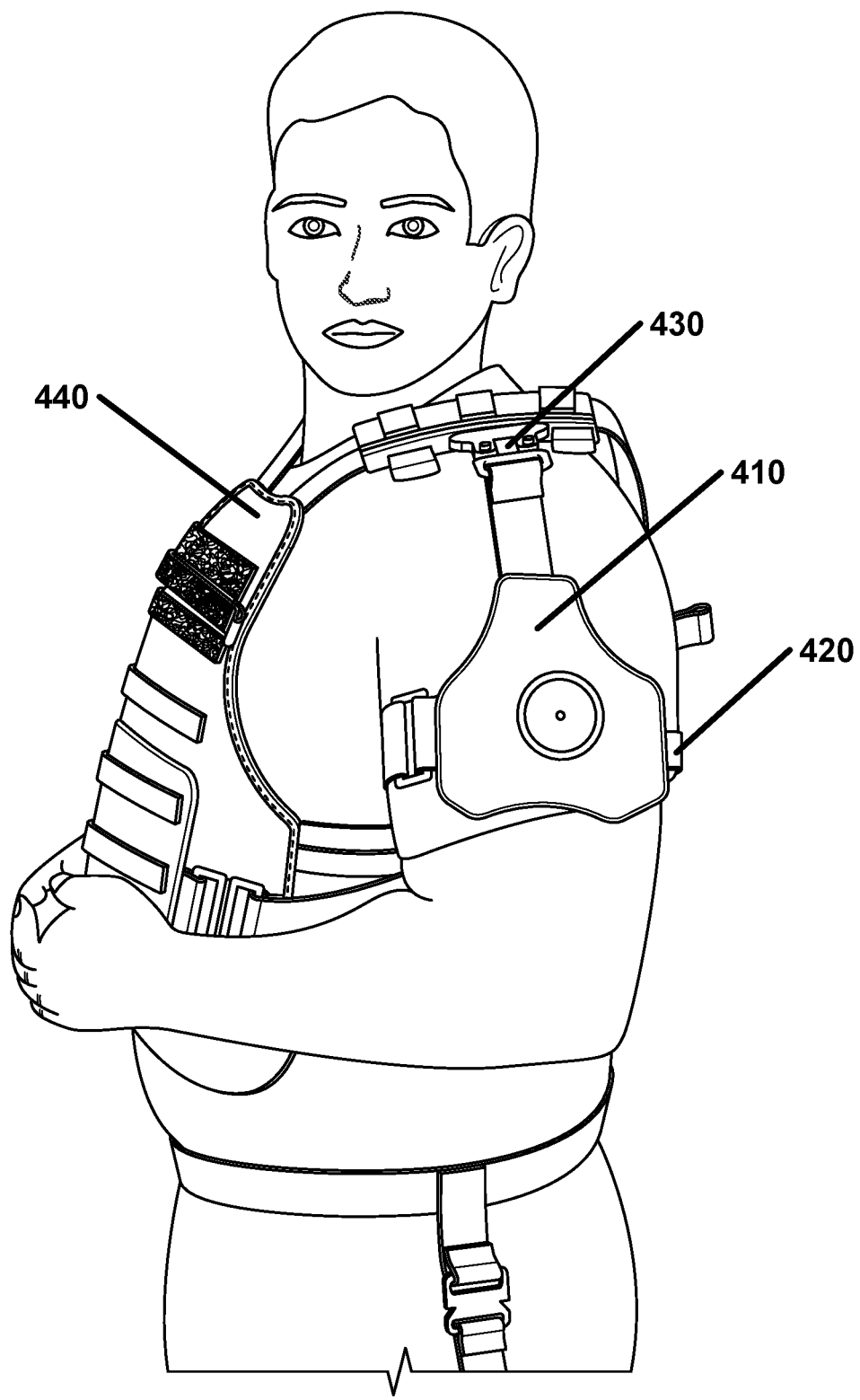
FIG. 4 illustrates an example wearable device attached to an example wearable item according to an aspect of an embodiment.

FIG. 4 illustrates an example wearable device 410 attached to an example wearable item 440 according to an aspect of an embodiment. The wearable device 410 may be attached to the wearable item 440 through employment of a wearable item quick release connector 430. The wearable item 440 may comprise body armor. The wearable device 410 may comprise a tourniquet. The Tourniquet may comprise a tunnel strap 420.

Figure 5:
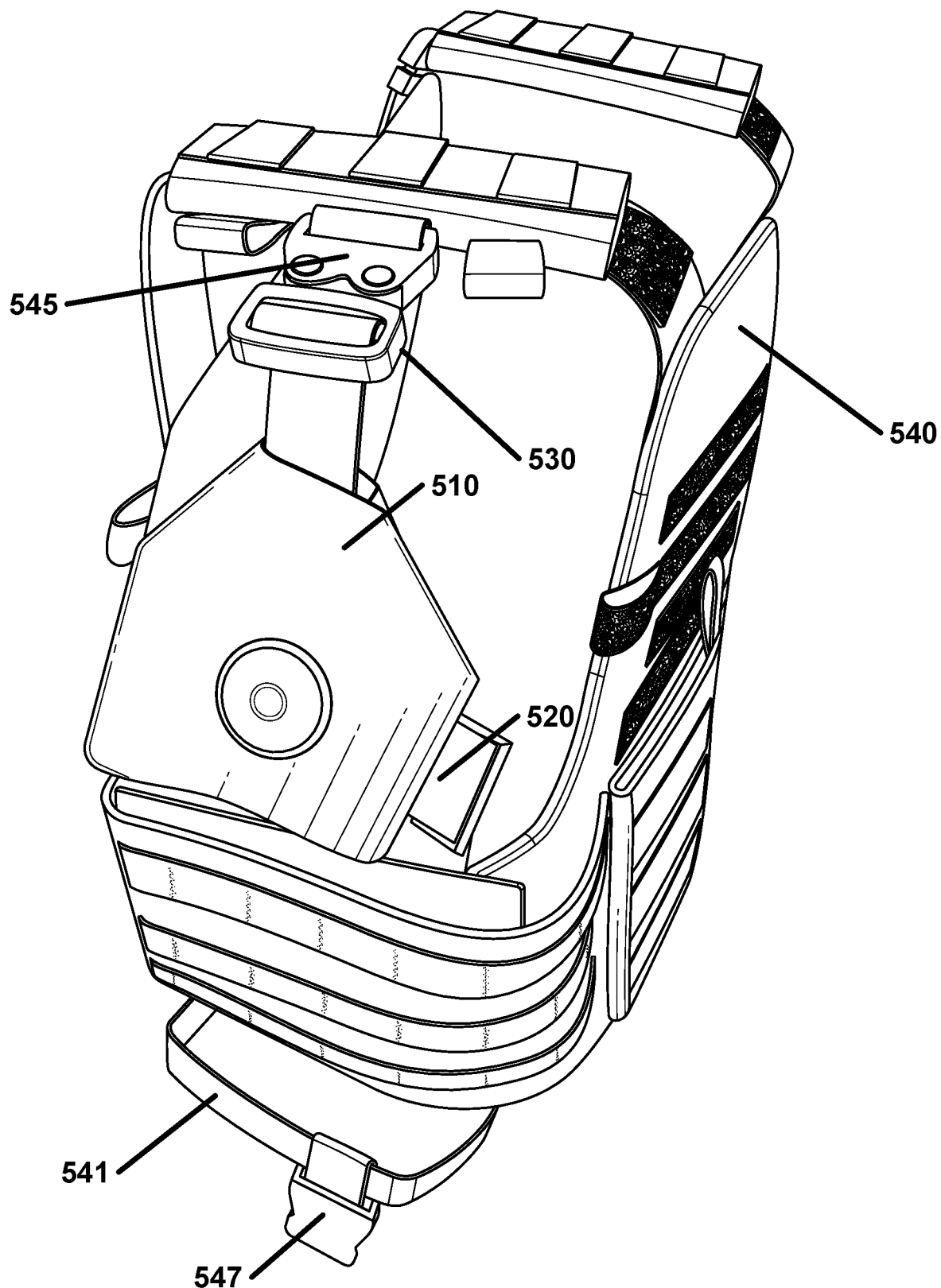
FIG. 5 illustrates an example wearable device attached to an example wearable item according to an aspect of an embodiment.

FIG. 5 illustrates an example wearable device 510 attached to an example wearable item 540 according to an aspect of an embodiment. The wearable device 510 may be attached to the wearable item 540 through employment of an example wearable item connector 545 and an example wearable item quick release connector 530. The wearable item 540 may comprise body armor. The wearable item 540 may comprise the wearable item connector 545. The wearable item connector 545 may be configured to connect to the wearable item quick release connector 530. The wearable device 510 may comprise a tourniquet. The Tourniquet may comprise tunnel strap 320. A second wearable item 541 may comprise a belt. The second wearable item 541 may comprise a second wearable item connector 547. The second wearable item connector 547 may be configured to receive a wearable item quick release connector (e.g. 132) of a second wearable device (e.g. 112).

Figure 6:
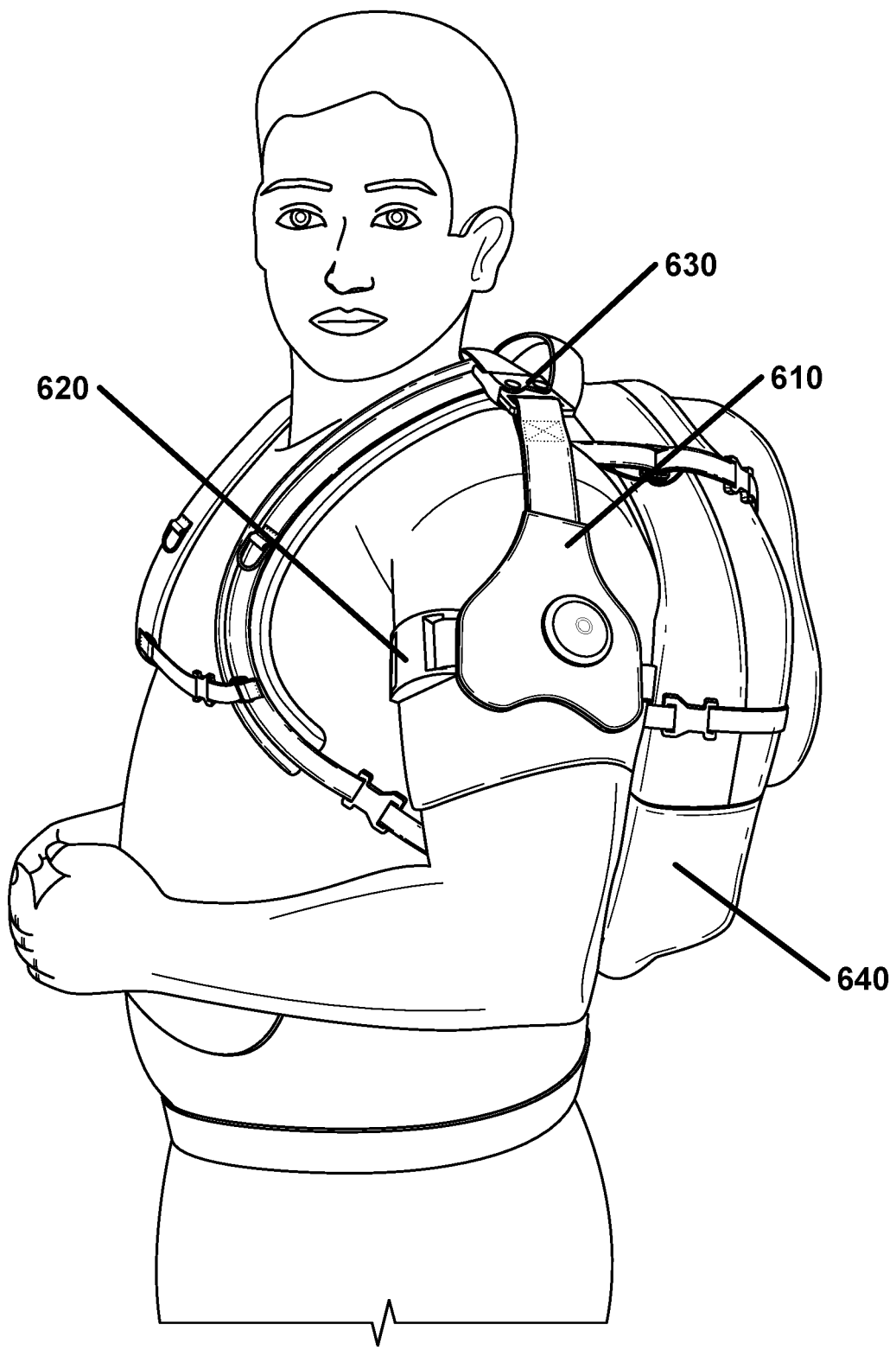
FIG. 6 illustrates an example wearable device attached to an example wearable item according to an aspect of an embodiment.

FIG. 6 illustrates an example wearable device 610 attached to an example wearable item 640 according to an aspect of an embodiment. The wearable device 610 may be attached to the wearable item 640 through employment of a wearable item quick release connector 630. The wearable item 640 may comprise body armor. The wearable device 610 may comprise a tourniquet. The Tourniquet may comprise a tunnel strap 620.

According to an embodiment, a wearable item may comprise a backpack. The backpack may comprise a rear ballistic plate carrier. The backpack may be structurally configured to connect to a deployable front ballistic plate carrier. The deployable front ballistic plate carrier may be deployed on the front of a wearer without impacting one or more connected tourniquets.

Figure 7:
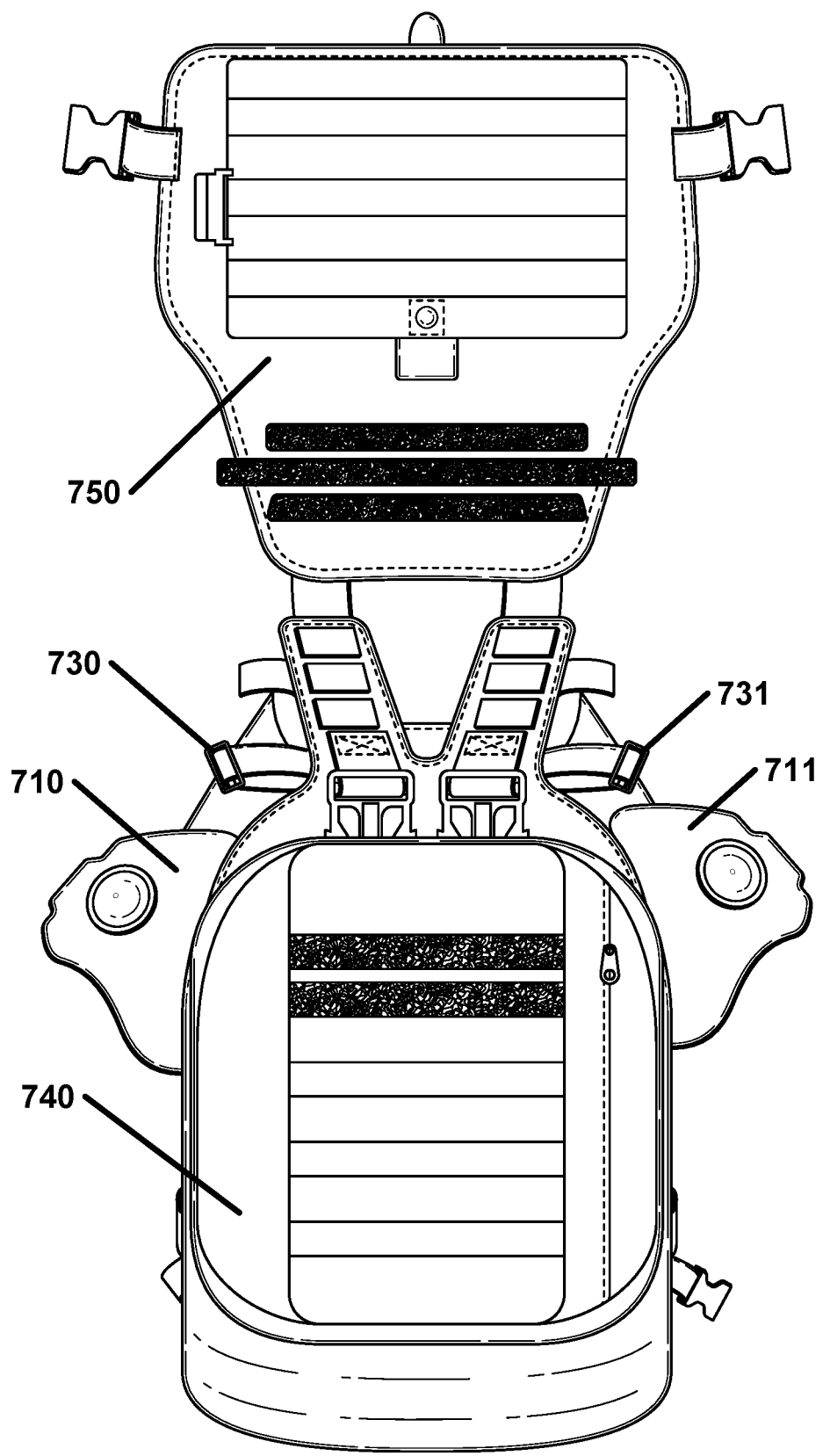
FIGS. 7 and 8 illustrate example wearable devices attached to an example backpack with an example deployable front ballistic plate carrier according to various aspects of various embodiments.
Figure 8:
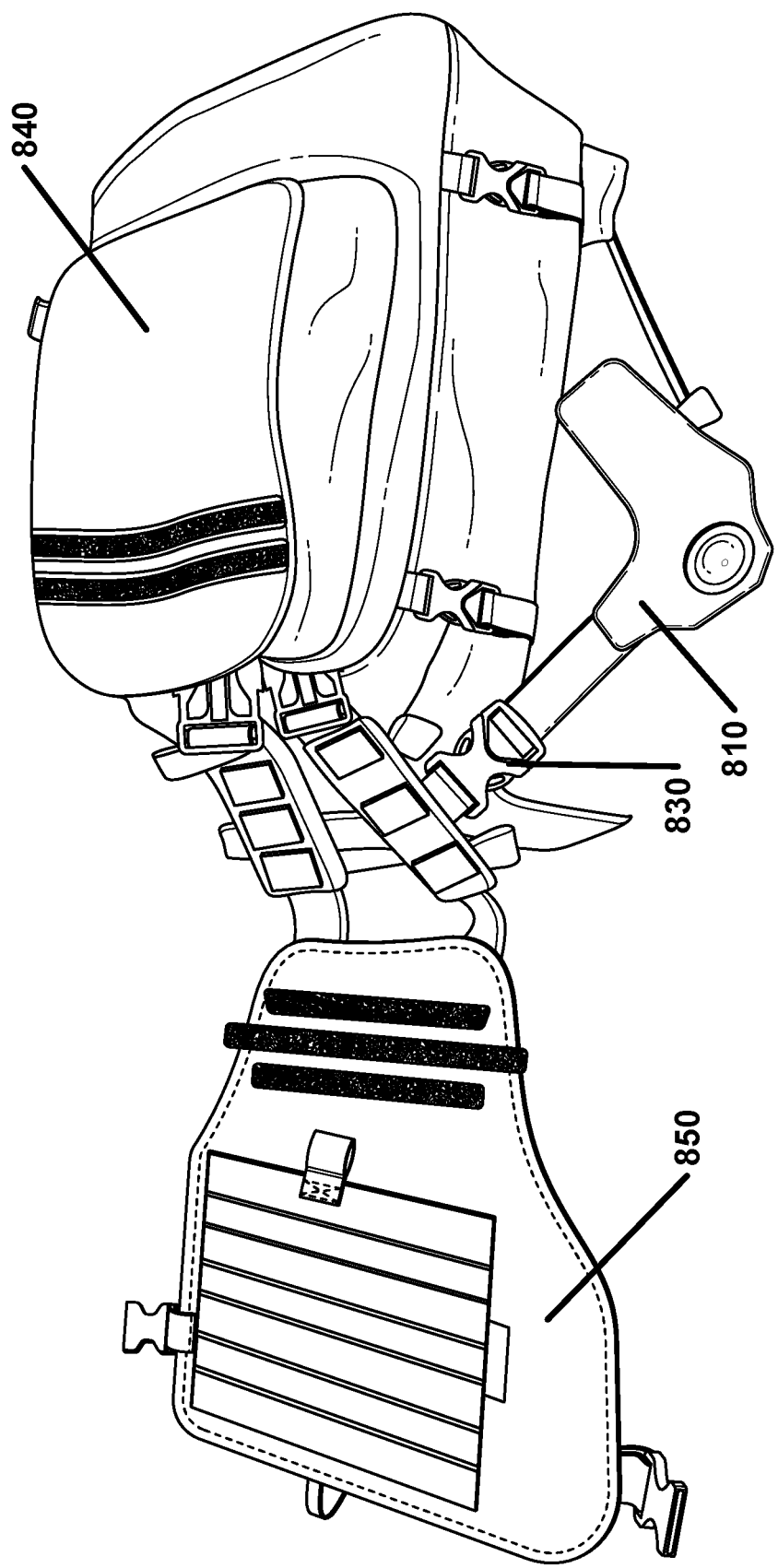

FIGS. 7 and 8 illustrate example wearable devices (710, 711, and 810) attached to an example backpack (740 and 840) with an example deployable front ballistic plate carrier (750 and 850) according to various aspects of various embodiments. The deployable front ballistic plate carrier (750 and 850) may be configured to be stowed in the backpack (740 and 840) until needed. The deployable front ballistic plate carrier (750 and 850) may be configured to be removably connected to the backpack (740 and 840). Each of the wearable devices (710, 711, and 810) may be attached to the backpack (740 and 840) through employment of a wearable item quick release connector (730, 731, and 830).

Figure 9:
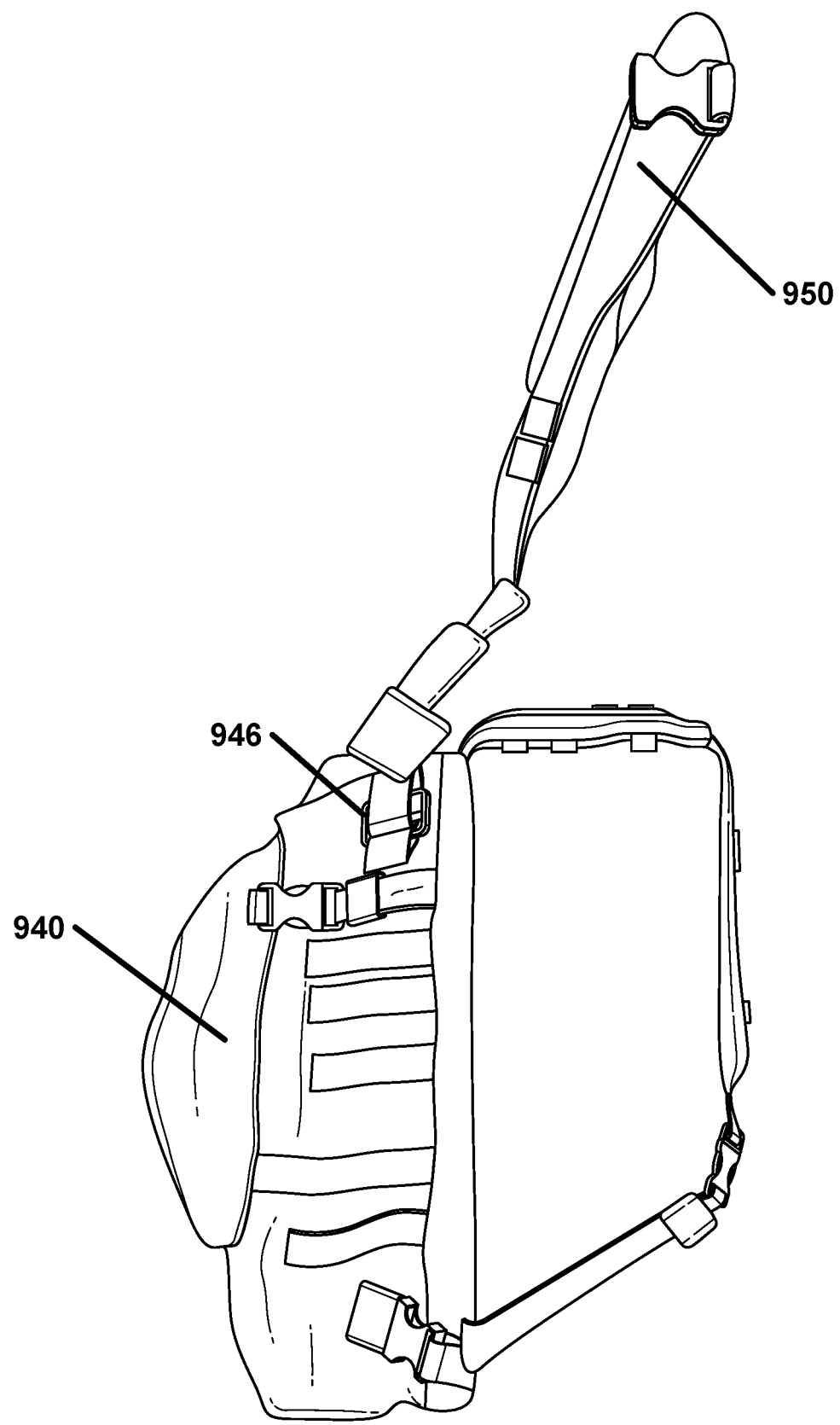
FIG. 9 illustrates an example backpack with an example deployable front ballistic plate carrier according to various aspects of various embodiments.

FIG. 9 illustrates an example backpack 940 with an example deployable front ballistic plate carrier 950 according to various aspects of various embodiments. The backpack may comprise a wearable item connector 946. The wearable item connector 946 may be configured to receive a wearable item quick release connector (e.g. 731) of a wearable device (e.g. 711).

Figure 10:
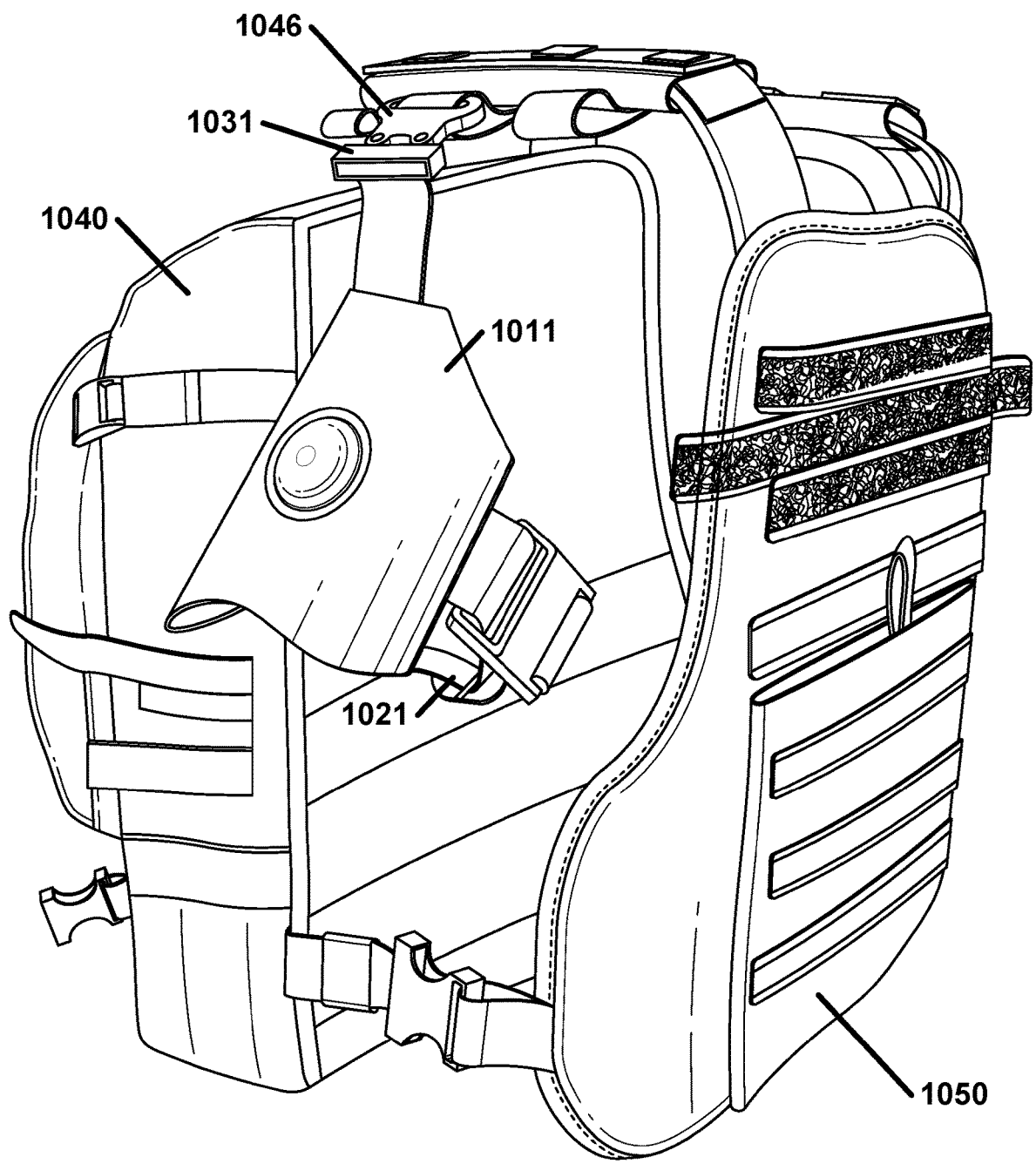
FIG. 10 illustrates an example backpack with an example deployable front ballistic plate carrier in a deployed position according to various aspects of various embodiments.

FIG. 10 illustrates an example backpack 1040 with an example deployable front ballistic plate carrier 1050 in a deployed position according to various aspects of various embodiments. An example wearable device 1011 may be attached to the backpack 1040 through employment of a wearable item quick release connector 1031. The backpack 1040 may comprise a wearable item connector 1046. The wearable item connector 1046 may be configured to connect to the wearable item quick release connector 1031. The wearable device 1011 may comprise a tourniquet. The tourniquet may comprise a tunnel strap 1021.

Figure 11:
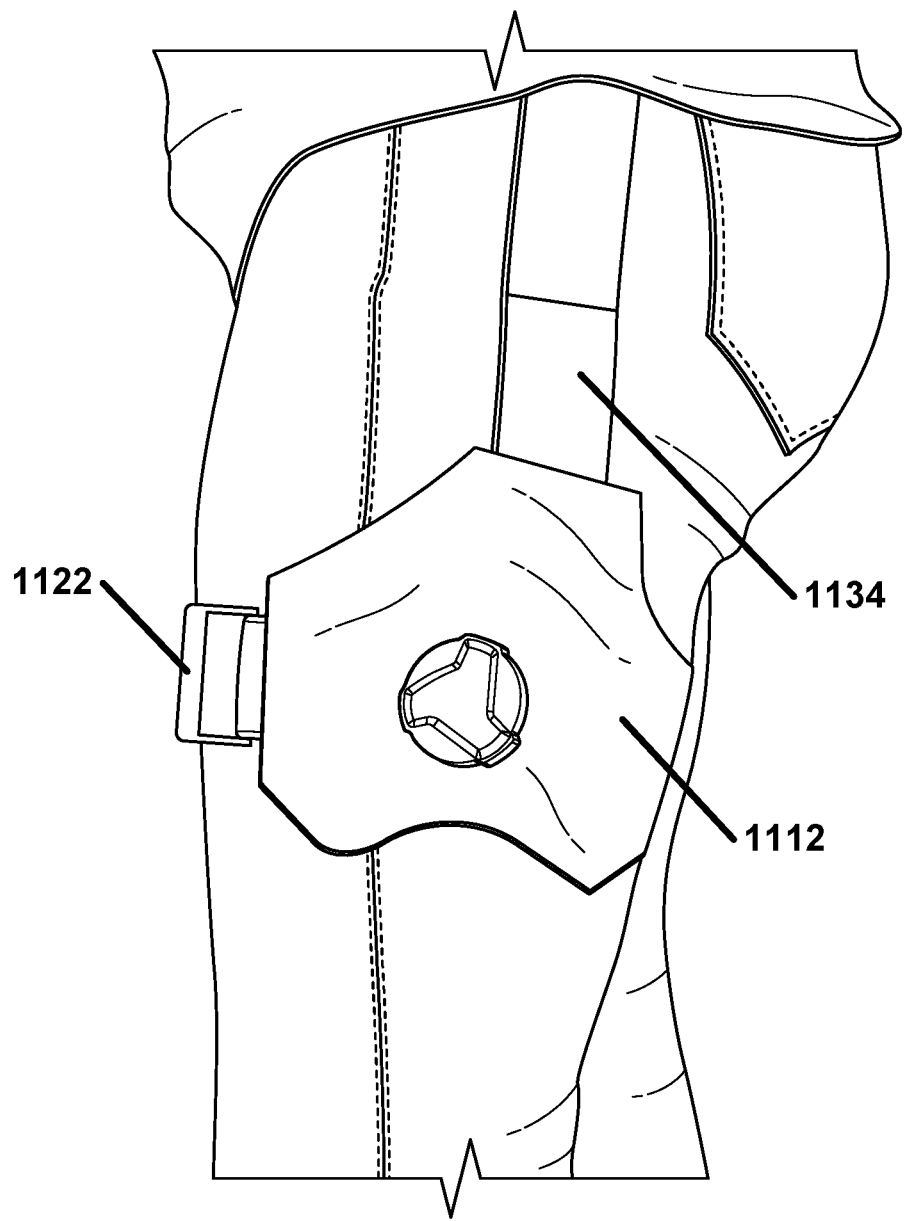
FIG. 11 illustrates an example wearable device attached to an example wearable item according to an aspect of an embodiment.

FIG. 11 illustrates an example wearable device 1112 attached to an example wearable item (e.g. 141, not shown) according to an aspect of an embodiment. The wearable device 1112 may comprise a wearable item strap 1134. The wearable item strap 1134 may be configured to removably connect to the wearable item (e.g. 141). The wearable item strap 1134 may comprise a hook and loop fastener. The wearable device 1112 may comprise a tourniquet. The tourniquet may comprise a tunnel strap 1122.

According to an embodiment, a tourniquet may comprise at least one base plate. The at least one base plate may be flexible. The at least one base plate may comprise a low friction material such as, for example, a homopolymer acetal. An example of a homopolymer acetal includes Delrin. The at least one base plate may comprise at least one recycled material. The at least one base plate may comprise at least one organic material such as, for example, Mycelium. The at least one base plate may comprise an ergonomic shape. The at least one base plate may be structurally configured for an arm and/or a leg of a wearer. The at least one base plate may be connected to two anchor points. The at least one base plate may comprise the two anchor points. One of the at least one base plate may be connected to a tightening mechanism. The tightening mechanism may comprise at least one organic material. Two laces may be employed to connect the tightening mechanism to a first end of a tunnel strap and the two anchor points. The two laces may, for example, comprise ultra-high molecular weight polyethylene fibers. The two laces may comprise at least one organic material. The first end of the tunnel strap may comprise two lace guides configured to guide the two laces. The two lace guides may comprise at least one organic material. The first end of the tunnel strap may be structurally configured to slide along the surface of at least one of the at least one base plate as the tightening mechanism is tightened. A second end of the tunnel strap may be structurally configured to connect to a second end of a fixed strap. The second end of the tunnel strap may be structurally configured to connect to the second end of the fixed strap through employment of a tunnel strap quick release connector. A first end of the fixed strap may be fastened to one of the at least one base plate. The first end of the fixed strap may be fastened to the one of the at least one base plate through employment of a single pivot. The fixed strap may be adjustable in length. Alternatively, the second end of the tunnel strap may be fastened directly to one of the at least one base plate. The second end of the tunnel strap may be fastened directly to the one of the at least one base plate through employment of a single pivot.

According to an embodiment, one of at least one base plate may be structurally configured to receive a second end of a tunnel strap. The second end of the tunnel strap may be received through employment of a tunnel strap loop connector. The tunnel strap loop connector may be connected to the one of the at least one base plate. The tunnel strap loop connector may be connected to the one of the at least one base plate through employment of a fixed strap. The tunnel strap loop connector may be integrated into the one of the at least one base plate.

According to an embodiment, a tunnel strap may comprise a hook and loop fastener. The hook and loop fastener may be sewn onto the tunnel strap. The hook and loop fastener may comprise alternating rows of hook material and loop material. This alternating hook and loop configuration may provide a greater range of adjustability over a standard configuration comprising one section of hook material and one section of loop material. The alternating hook and loop configuration may enable a user to store a tourniquet with a second end of a tunnel strap connected to a tunnel strap loop connector. The alternating hook and loop configuration may prevent the tunnel strap from separating from the tunnel strap loop connector during the donning of the tourniquet. The alternating hook and loop configuration may enable a user to adjust the length of the tunnel strap with one hand. The tunnel strap may be adjusted to allow for donning the tourniquet over an extremity and clothing, if necessary. The alternating hook and loop configuration may enable a wearer to wear a wearable device on an extremity without occluding blood flow. In the case the wearer sustains a hemorrhage on the extremity, the tunnel strap may be configured for quick and easy application through employment of the alternating hook and loop configuration when the tunnel strap is already connected to the tunnel strap loop connector.

Figure 12:
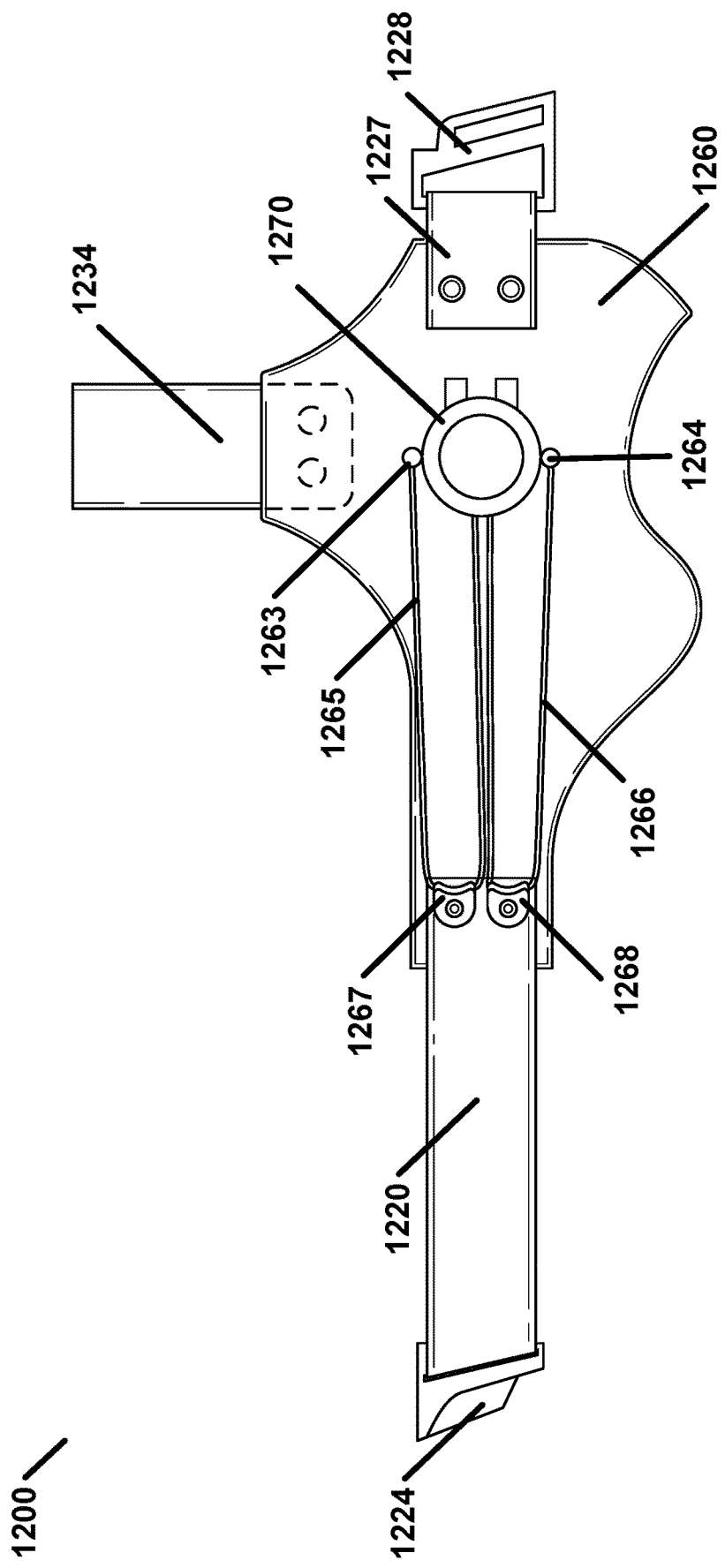
FIG. 12 illustrates an example wearable device according to an aspect of an embodiment.

FIG. 12 illustrates an example wearable device 1200 according to an aspect of an embodiment. The wearable device 1200 may comprise a tourniquet. The tourniquet may comprise at least one base plate 1260. The tourniquet may comprise two anchor points (1263 and 1264). The tourniquet may comprise two laces (1265 and 1266). The tourniquet may comprise a tunnel strap 1220. The tunnel strap 1220 may comprise two lace guides (1267 and 1268) connected to a first end of the tunnel strap 1220. The tourniquet may comprise a fixed strap 1227. The tourniquet may comprise a first part of a tunnel strap quick release connector 1228 connected to the fixed strap 1227. The tourniquet may comprise a second part of a tunnel strap quick release connector 1224 connected to the tunnel strap 1220. The first part of the tunnel strap quick release connector 1228 may be configured to connect to the second part of the tunnel strap quick release connector 1224. The tourniquet may comprise a tightening mechanism 1270. The tourniquet may comprise a specific lacing pattern comprising the location of the two anchor points (1263 and 1264) in relation to the location of the two lace guides (1267 and 1268) and the location of the tightening mechanism 1270. The wearable device 1200 may comprise a wearable item quick release connector. The wearable item quick release connector may be connected to the tourniquet through employment of a wearable item strap 1234. The wearable item quick release connector may be configured to removably connect to a wearable item. The wearable device 1200 may comprise a wearable item loop connector. The wearable item loop connector may be connected to the tourniquet through employment of the wearable item strap 1234. The wearable item loop connector may be configured to removably connect to the wearable item.

Figure 13:
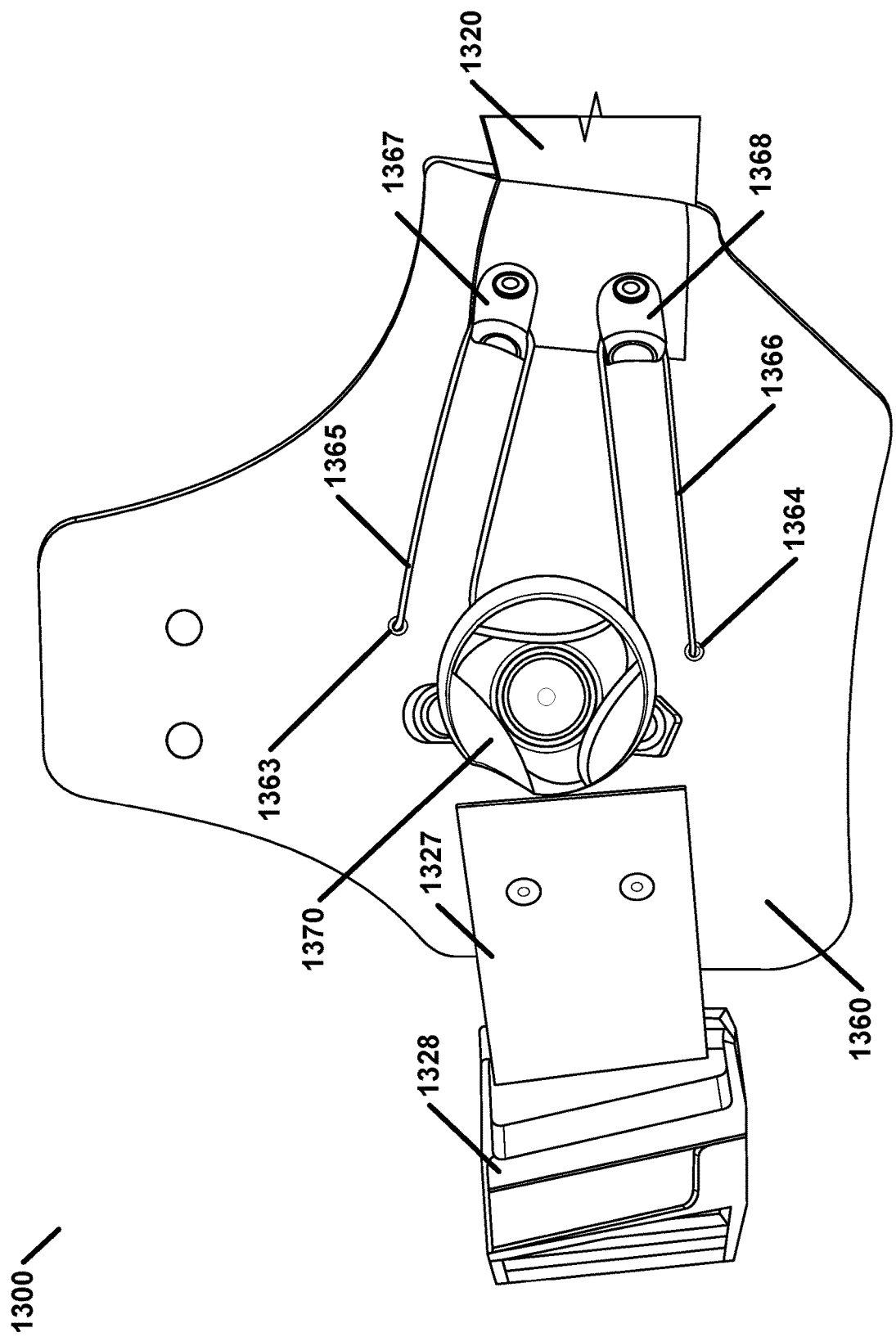
FIG. 13 illustrates an example tourniquet according to an aspect of an embodiment.

FIG. 13 illustrates an example tourniquet 1300 according to an aspect of an embodiment. The tourniquet 1300 may comprise at least one base plate 1360. The tourniquet 1300 may comprise two anchor points (1363 and 1364). The tourniquet 1300 may comprise two laces (1365 and 1366). The tourniquet 1300 may comprise a tunnel strap 1320. The tunnel strap 1320 may comprise two lace guides (1367 and 1368) connected to a first end of the tunnel strap 1320. The tourniquet 1300 may comprise a fixed strap 1327. The tourniquet 1300 may comprise a tunnel strap quick release connector 1328 connected to the fixed strap 1327. The tunnel strap quick release connector 1328 may be configured to receive a second end of the tunnel strap 1320. The tourniquet 1300 may comprise a tightening mechanism 1370. The tourniquet 1300 may comprise a specific lacing pattern comprising the location of the two anchor points (1363 and 1364) in relation to the location of the two lace guides (1367 and 1368) and the location of the tightening mechanism 1370.

Figure 14:
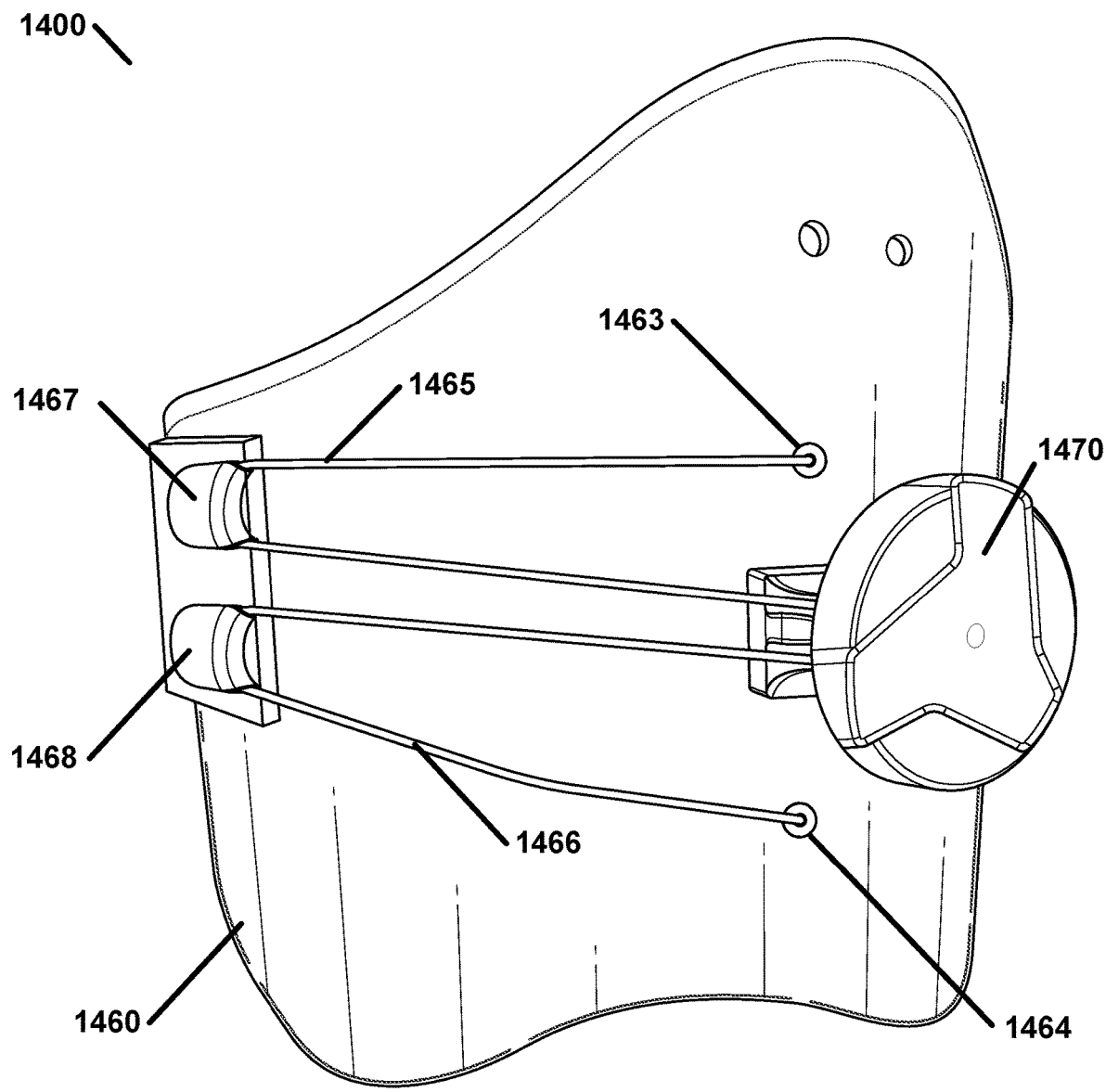
FIG. 14 illustrates an example tourniquet according to an aspect of an embodiment.

FIG. 14 illustrates an example tourniquet 1400 according to an aspect of an embodiment. The tourniquet 1400 may comprise at least one base plate 1460. The tourniquet 1400 may comprise two anchor points (1463 and 1464). The tourniquet 1400 may comprise two laces (1465 and 1466). The tourniquet 1400 may comprise a tunnel strap. The tunnel strap may comprise two lace guides (1467 and 1468) connected to a first end of the tunnel strap. The tourniquet 1400 may comprise a tightening mechanism 1470. The tourniquet 1400 may comprise a specific lacing pattern comprising the location of the two anchor points (1463 and 1464) in relation to the location of the two lace guides (1467 and 1468) and the location of the tightening mechanism 1470.

According to an embodiment, a tourniquet may comprise an outer cuff. The outer cuff may be structurally configured to cover at least a portion of at least one base plate.

According to an embodiment, an outer cuff may be interchangeable. A plurality of distinct outer cuffs may comprise a plurality of distinct patterns. For example, distinct patterns may comprise a specific camouflage pattern and/or a specific set of camouflage colors. The outer cuff may be structurally configured to cover at least a portion of at least one base plate of a tourniquet. The outer cuff may be structurally configured to cover at least a portion of a tunnel strap of the tourniquet. The outer cuff may be structurally configured to cover at least a portion of two laces of the tourniquet. The outer cuff may comprise one or more fasteners. The one or more fasteners may comprise a snap, a zipper, a hook and loop fastener, combinations thereof, and/or the like.

Figure 15A:
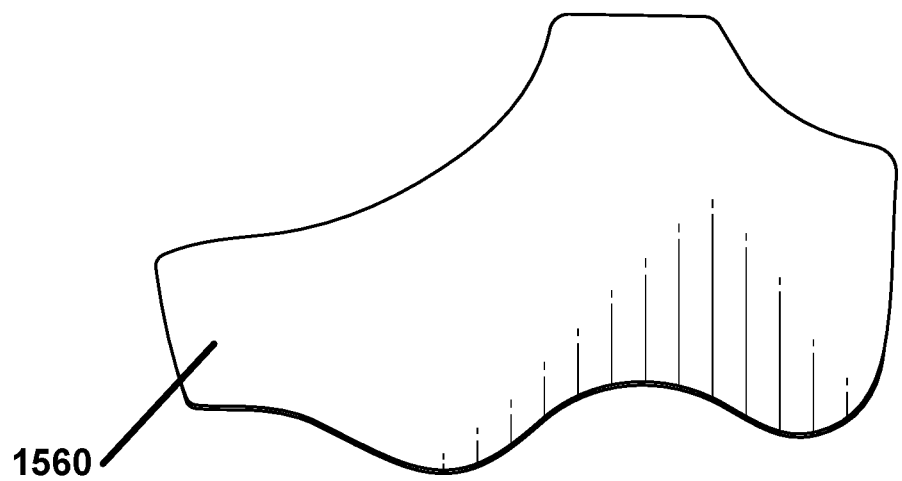
FIG. 15A illustrates an example base plate of an example tourniquet according to an aspect of an embodiment.

FIG. 15A illustrates an example base plate 1560 of an example tourniquet according to an aspect of an embodiment. The base plate 1560 may comprise an ergonomic shape. The ergonomic shape may be configured to enable a wearer of the tourniquet to maintain range of motion of an extremity. The ergonomic shape may be configured to provide comfort to a wearer when the tourniquet is worn prior to sustaining an injury.

Figure 15B:
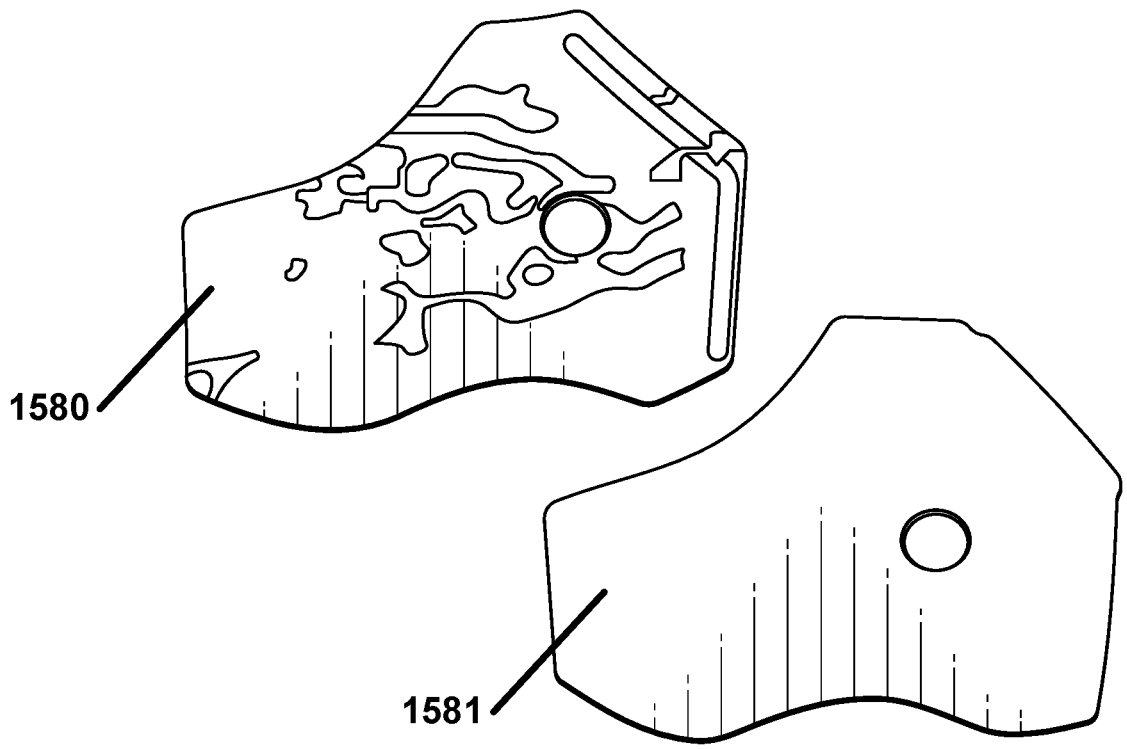
FIG. 15B illustrates two example interchangeable outer cuffs for an example tourniquet according to an aspect of various embodiments.

FIG. 15B illustrates two example interchangeable outer cuffs (1580 and 1581) for an example tourniquet according to an aspect of various embodiments. An interchangeable outer cuff 1580 may comprise a camouflage pattern. An interchangeable outer cuff 1581 may comprise a solid pattern.

Figure 16:
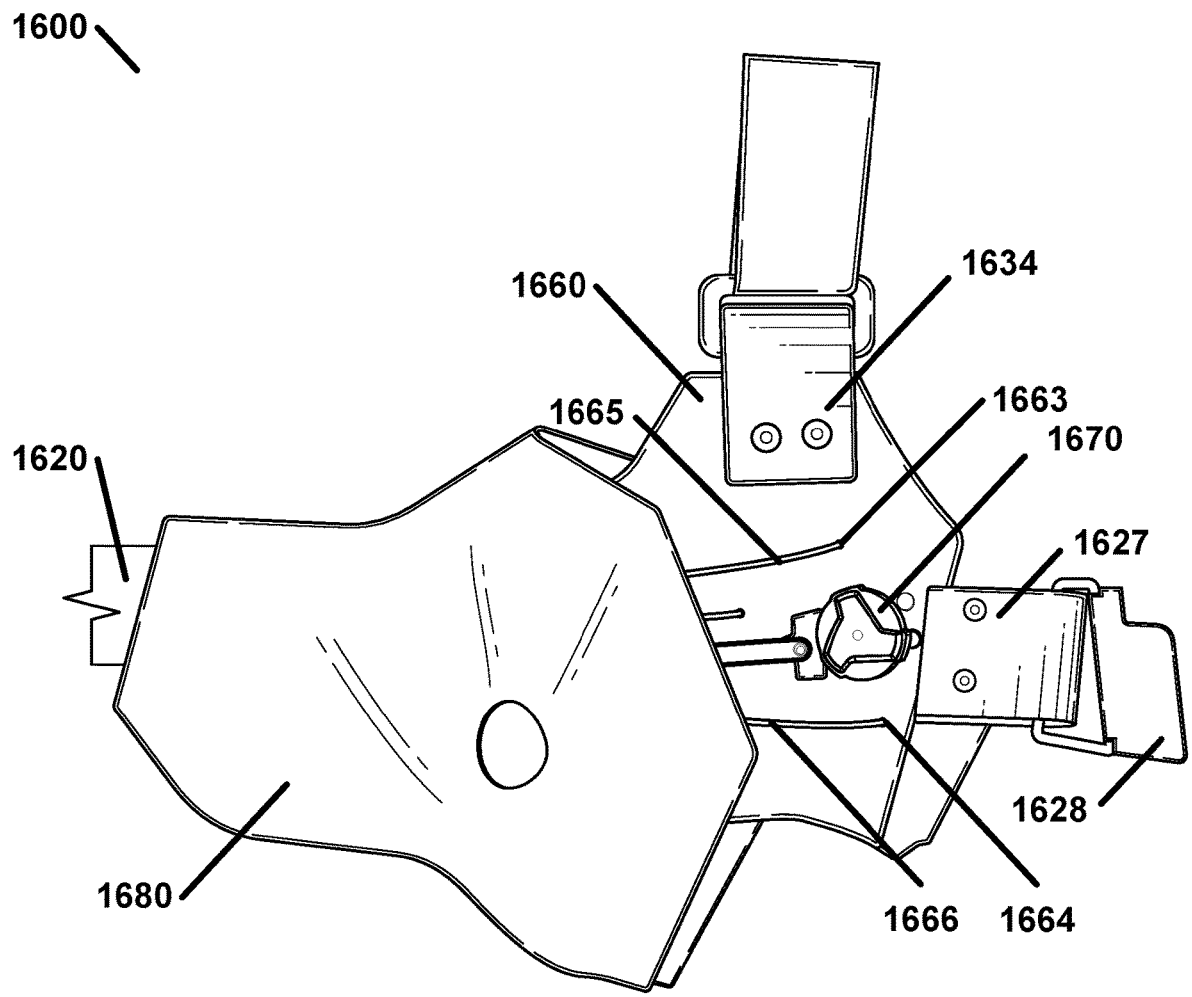
FIG. 16 illustrates an example wearable device partially inserted into an example outer cuff according to an aspect of an embodiment.

FIG. 16 illustrates an example wearable device 1600 partially inserted into an example outer cuff 1680 according to an aspect of an embodiment. The wearable device 1600 may comprise a tourniquet. The tourniquet may comprise at least one base plate 1660. The tourniquet may comprise two anchor points (1663 and 1664). The tourniquet may comprise two laces (1665 and 1666). The tourniquet may comprise a tunnel strap 1620. The tunnel strap 1620 may comprise two lace guides connected to a first end of the tunnel strap 1620. The tourniquet may comprise a fixed strap 1627. The tourniquet may comprise a first part of a tunnel strap quick release connector 1628 connected to the fixed strap 1627. The tourniquet may comprise a tightening mechanism 1670. The wearable device 1600 may comprise a wearable item quick release connector. The wearable item quick release connector may be connected to the tourniquet through employment of a wearable item strap 1634. The wearable item quick release connector may be configured to removably connect to a wearable item. The first end of the tunnel strap 1620 may be connected to the tightening mechanism 1670 through employment of the two laces (1665 and 1666) routed through the two lace guides. The first end of the tunnel strap 1620 may not be otherwise connected to the at least one base plate 1660. Therefore, the outer cuff 1680 may be employed to locate the first end of the tunnel strap 1620 on the exterior side (as shown) of the at least one base plate 1660. The first end of the tunnel strap 1620 may be configured to slide along the exterior side of the at least one base plate 1660. At least a portion of the exterior side of the at least one base plate 1660 may comprise at least one low friction material.

Figure 17A:
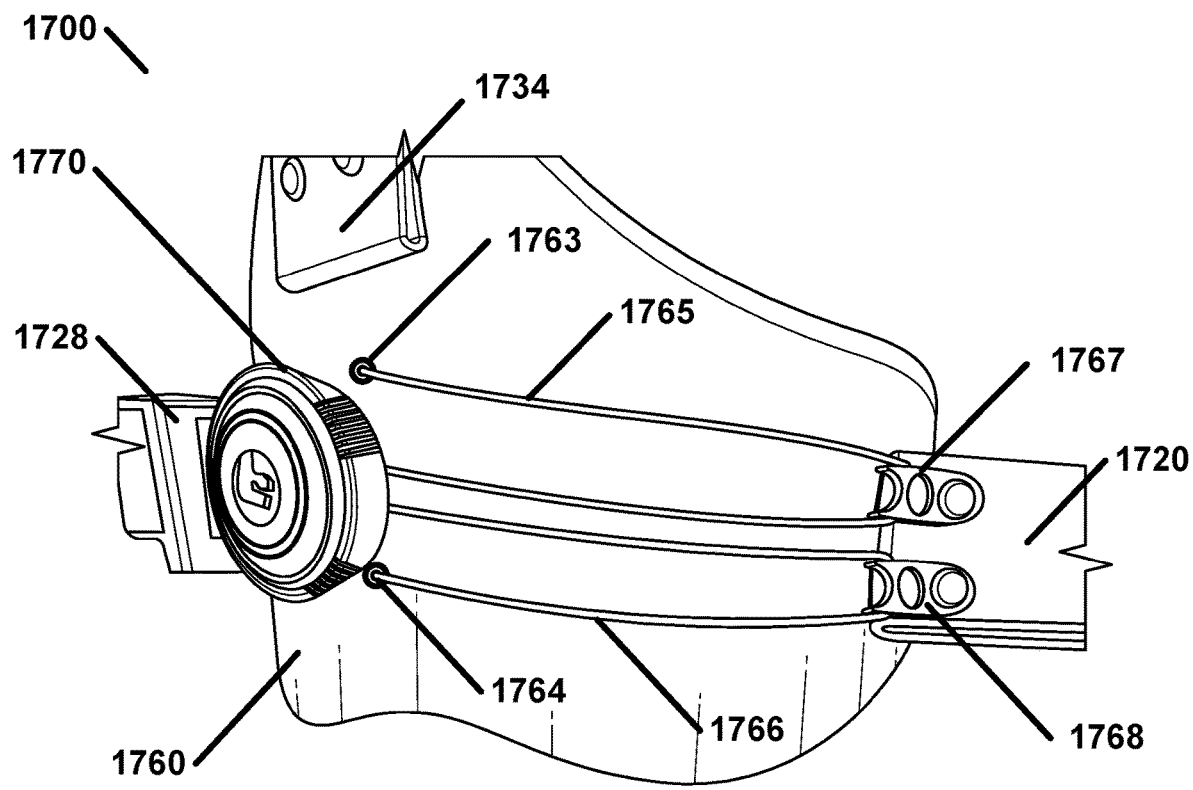
FIG. 17A illustrates an example wearable device according to an aspect of an embodiment.

FIG. 17A illustrates an example wearable device 1700 according to an aspect of an embodiment. The wearable device 1700 may comprise a tourniquet. The tourniquet may comprise at least one base plate 1760. The tourniquet may comprise two anchor points (1763 and 1764). The tourniquet may comprise two laces (1765 and 1766). The tourniquet may comprise a tunnel strap 1720. The tunnel strap 1720 may comprise two lace guides (1767 and 1768) connected to a first end of the tunnel strap 1720. The tourniquet may comprise a fixed strap. The tourniquet may comprise a first part of a tunnel strap quick release connector 1728 connected to the fixed strap. The tourniquet may comprise a second part of a tunnel strap quick release connector, not shown, connected to the tunnel strap 1720. The tourniquet may comprise a tightening mechanism 1770. The tourniquet may comprise a specific lacing pattern comprising the location of the two anchor points (1763 and 1764) in relation to the location of the two lace guides (1767 and 1768) and the location of the tightening mechanism 1770. The wearable device 1700 may comprise a wearable item quick release connector, not shown. The wearable item quick release connector may be connected to the tourniquet through employment of a wearable item strap 1734. The wearable item quick release connector may be configured to removably connect to a wearable item.

Figure 17B:
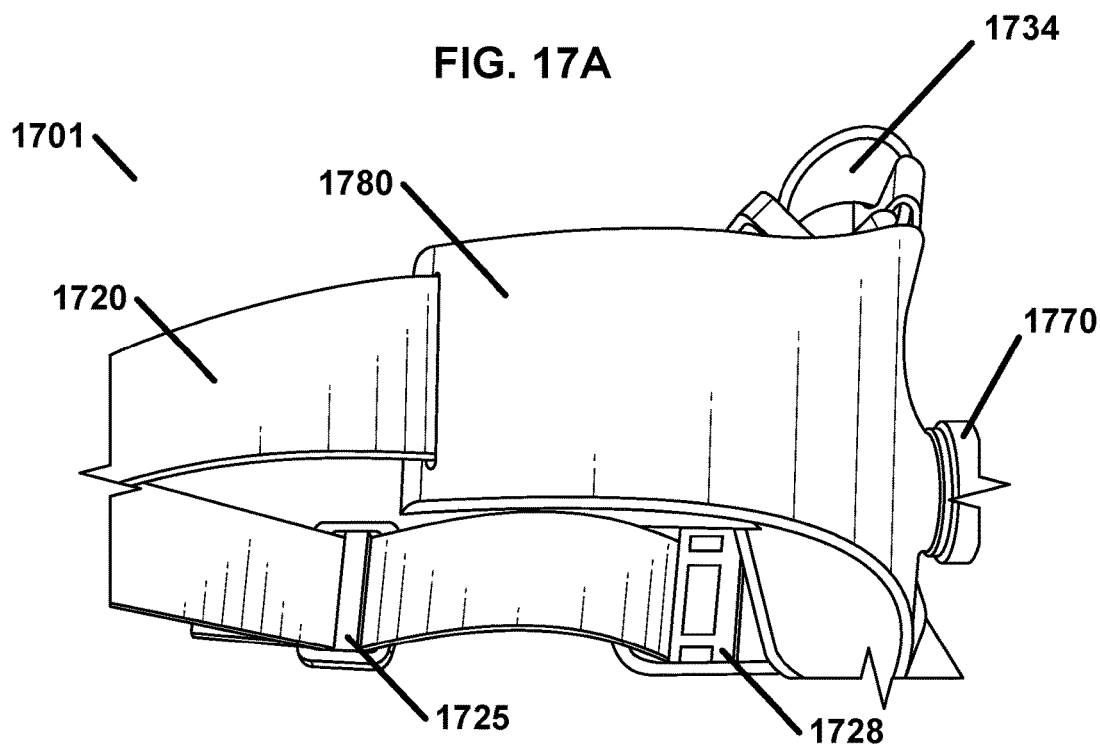
FIG. 17B illustrates an example tunnel strap sliding under an example outer cuff of an example wearable device according to an aspect of various embodiments.

FIG. 17B illustrates an example tunnel strap 1720 sliding under an example outer cuff 1780 of an example wearable device 1701 according to an aspect of various embodiments. The wearable device 1701 may comprise a tourniquet. The tourniquet may comprise the tunnel strap 1720. The tourniquet may comprise a tunnel strap quick release connector 1728 connected to the tunnel strap 1720. The length of the tunnel strap 1720 may be adjusted through employment of a slide lock buckle 1725. The tourniquet may comprise a tightening mechanism 1770. The wearable device 1701 may comprise a wearable item quick release connector. The wearable item quick release connector may be connected to the tourniquet through employment of a wearable item strap 1734.

Figure 18:
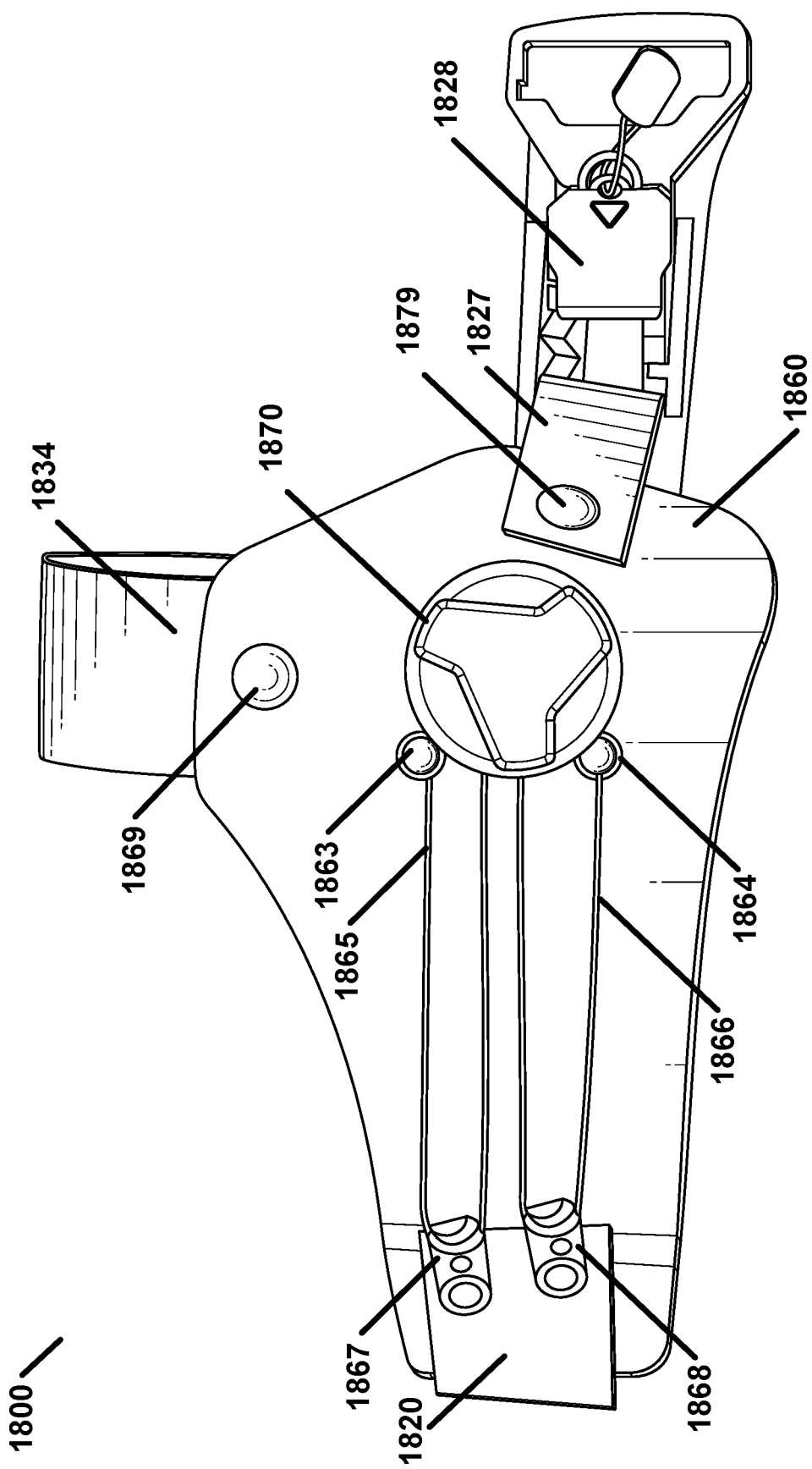
FIG. 18 illustrates an example wearable device according to an aspect of an embodiment.

FIG. 18 illustrates an example wearable device 1800 according to an aspect of an embodiment. The wearable device 1800 may comprise a tourniquet. The tourniquet may comprise at least one base plate 1860. The tourniquet may comprise two anchor points (1863 and 1864). The tourniquet may comprise two laces (1865 and 1866). The tourniquet may comprise a tunnel strap 1820. The tunnel strap 1820 may comprise two lace guides (1867 and 1868) connected to a first end of the tunnel strap 1820. The tourniquet may comprise a fixed strap 1827. The fixed strap 1827 may be connected to one of the at least one base plate 1860 through employment of a single fixed strap pivot 1879. The tourniquet may comprise a tunnel strap quick release connector 1828 connected to the fixed strap 1827. The tunnel strap quick release connector 1828 may be configured to receive a second end of the tunnel strap 1820. The tunnel strap quick release connector 1828 may be adjustable. The tourniquet may comprise a tightening mechanism 1870. The tourniquet may comprise a specific lacing pattern comprising the location of the two anchor points (1863 and 1864) in relation to the location of the two lace guides (1867 and 1868) and the location of the tightening mechanism 1870. The wearable device 1800 may comprise a wearable item quick release connector. The wearable item quick release connector may be connected to the tourniquet through employment of a wearable item strap 1834. The wearable item strap may be connected to one of the at least one base plate 1860 through employment of a single wearable item strap pivot 1869.

According to an embodiment, a first of at least one base plate may be connected to a second of the at least one base plate through employment of a first hinge. A first part of the first hinge may be integrated into the first base plate. A second part of the first hinge may be integrated into the second base plate. The first hinge may be activated through employment of at least one first hinge spring. The second of the at least one base plate may be connected to a third of the at least one base plate through employment of a second hinge. A first part of the second hinge may be integrated into the second base plate. A second part of the second hinge may be integrated into the third base plate. The second hinge may be activated through employment of at least one second hinge spring.

According to an embodiment, a tightening mechanism may comprise a housing. The housing may be structurally configured to house at least a portion of a spool. The housing may be structurally configured to house at least a portion of two laces. The housing may be part of one of at least one base plate. In this example, the housing and the one of the at least one base plate may be one integrated part.

Figure 19A:
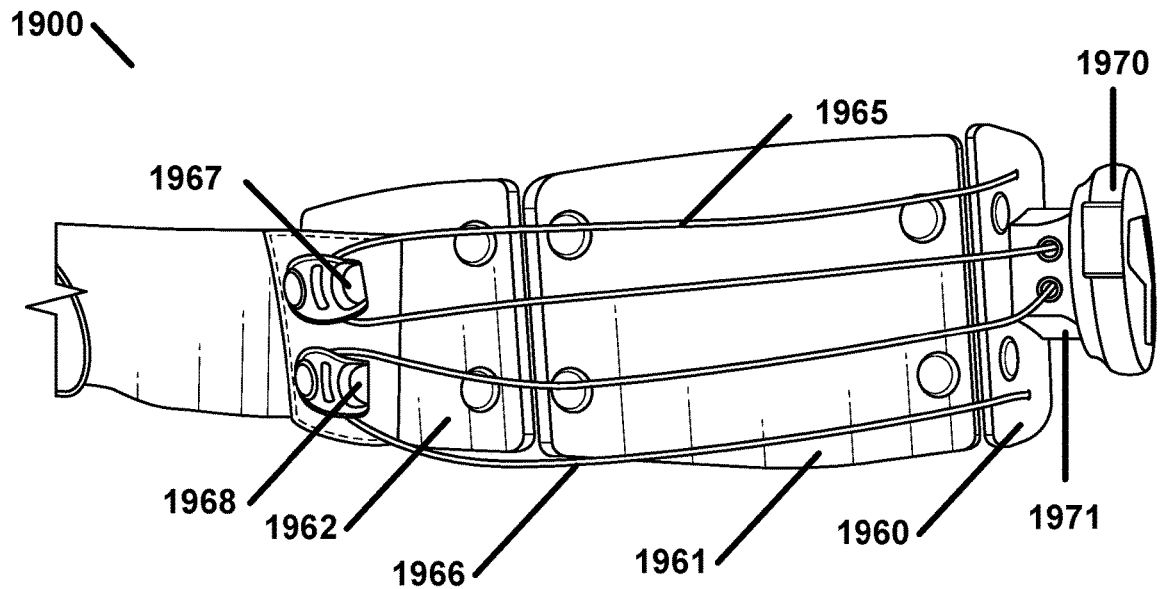
FIGS. 19A and 19B illustrate an example tourniquet with a plurality of base plates according to various aspects of an embodiment.
Figure 19B:
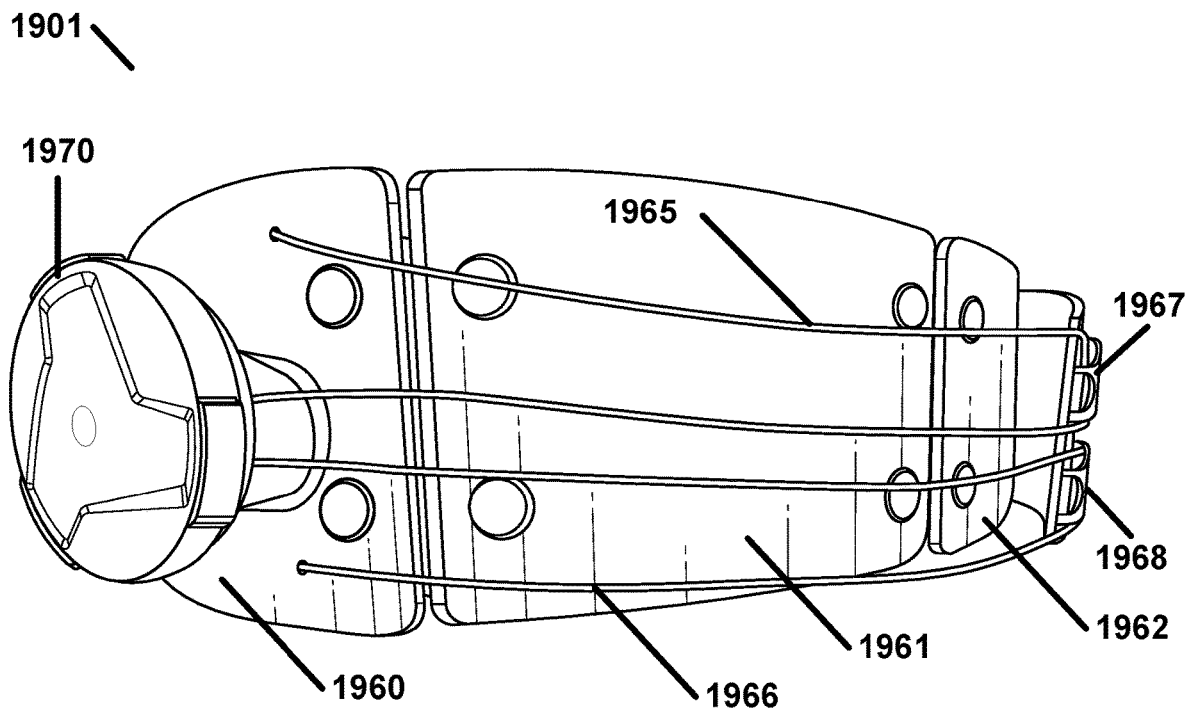

FIGS. 19A and 19B illustrate an example tourniquet (1900 and 1901) with a plurality of base plates (1960, 1961, and 1962) according to various aspects of an embodiment. The tourniquet (1900 and 1901) may comprise the plurality of base plates (1960, 1961, and 1962). The tourniquet (1900 and 1901) may comprise two laces (1965 and 1966). The tourniquet (1900 and 1901) may comprise a tunnel strap. The tunnel strap may comprise two lace guides (1967 and 1968) connected to a first end of the tunnel strap. The tourniquet (1900 and 1901) may comprise a tightening mechanism 1970. The tightening mechanism 1970 may comprise a housing 1971. The housing 1971 may be integrated with one of the at least one base plate (e.g. 1960).

Figure 20A:
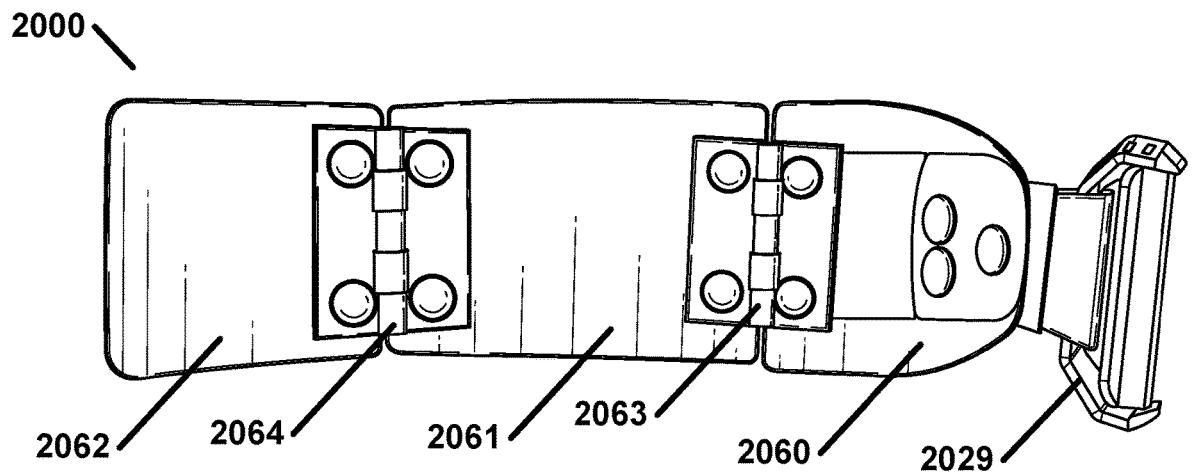
FIG. 20A illustrates an example tourniquet with a plurality of base plates in an open position according to an aspect of an embodiment.

FIG. 20A illustrates an example tourniquet 2000 with a plurality of base plates (2060, 2061, and 2062) in an open position according to an aspect of an embodiment. The tourniquet 2000 may comprise the plurality of base plates (2060, 2061, and 2062). The plurality of base plates (2060, 2061, and 2062) may be connected through employment of at least one hinge (2063 and 2064). The tourniquet 2000 may comprise a tunnel strap loop connector 2029.

Figure 20B:
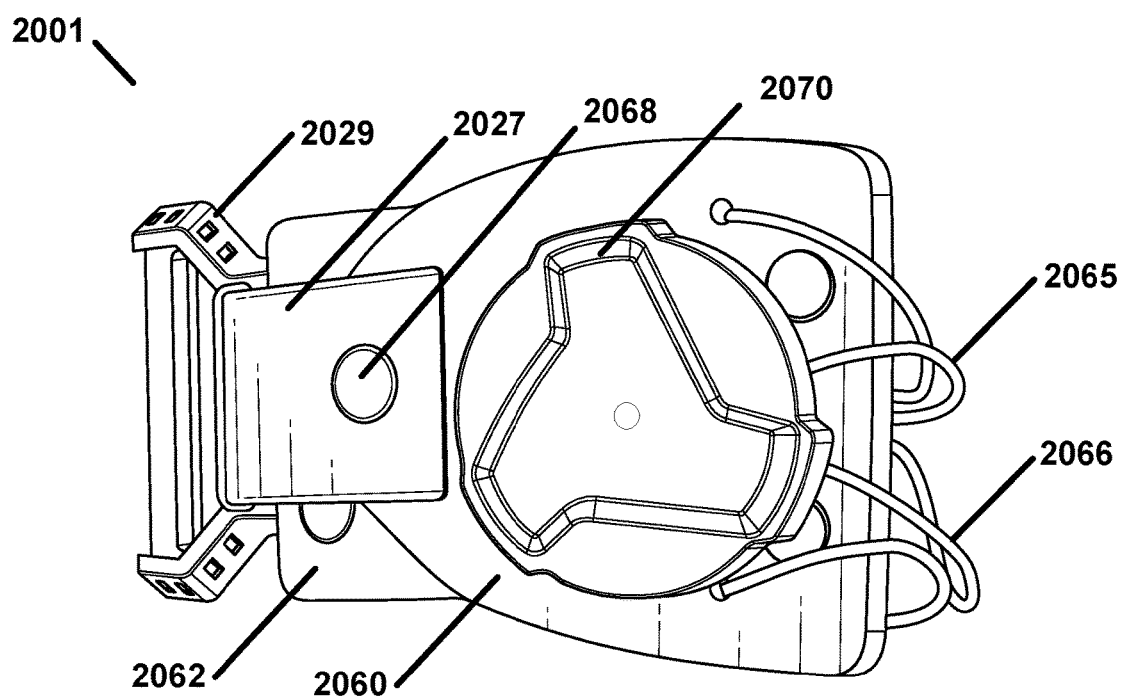
FIG. 20B illustrates an example tourniquet with a plurality of base plates in a folded position according to an aspect of an embodiment.

FIG. 20B illustrates an example tourniquet 2001 with a plurality of base plates (2060, 2061 (not shown), and 2062) in a folded position according to an aspect of an embodiment. The tourniquet 2001 may comprise the plurality of base plates (2060, 2061 (not shown), and 2062). The tourniquet 2001 may comprise two laces (2065 and 2066). The tourniquet 2001 may comprise a tunnel strap loop connector 2029. The tunnel strap loop connector 2029 may be connected to one of the plurality of base plates (e.g. 2060) through employment of a fixed strap 2027. The fixed strap 2027 may be connected to one of the at least one base plate (e.g. 2060) through employment of a single fixed strap pivot 2068. The tourniquet 2001 may comprise a tightening mechanism 2070.

Figure 21:
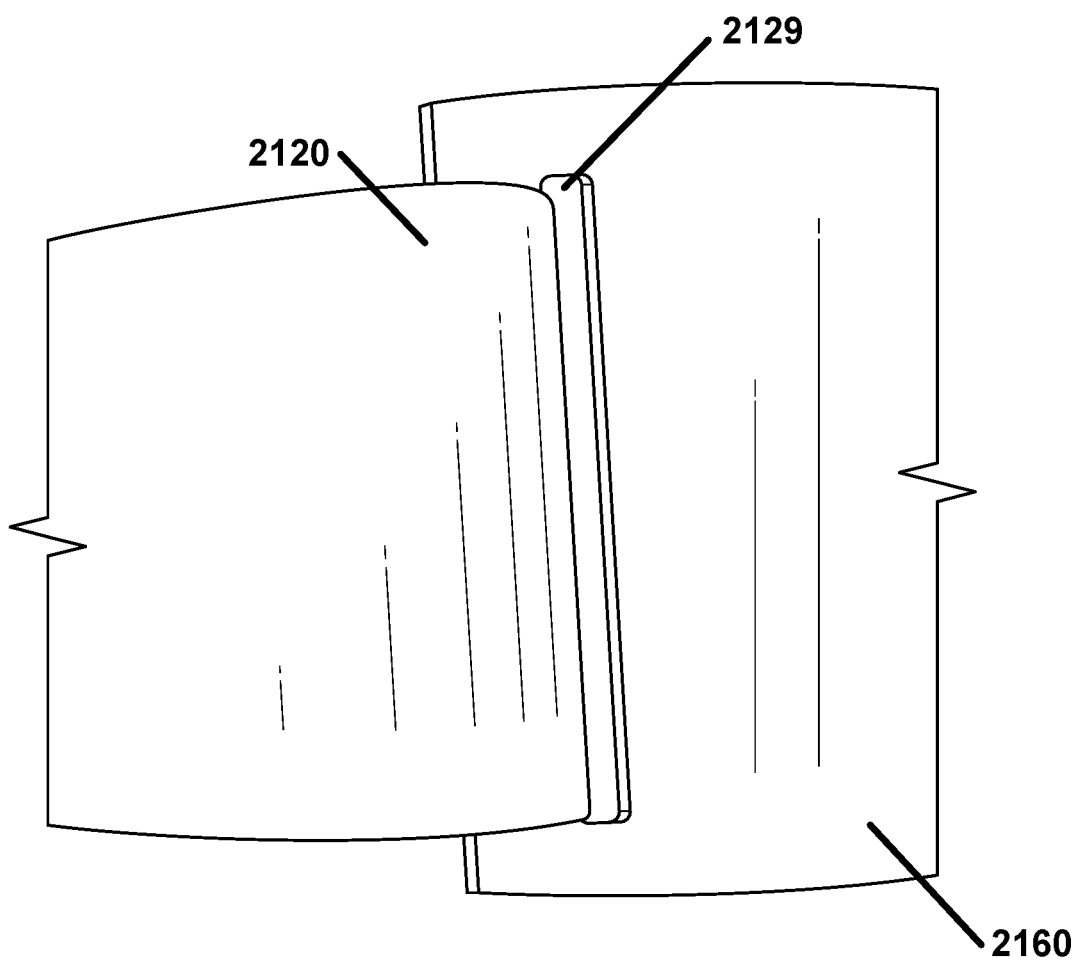
FIG. 21 illustrates an example tunnel strap loop connector of an example base plate according to an aspect of an embodiment.

FIG. 21 illustrates an example tunnel strap loop connector 2129 of an example base plate 2160 according to an aspect of an embodiment. The tunnel strap loop connector 2129 may be integrated into the base plate 2160. The tunnel strap loop connector 2129 may be configured to receive a second end of a tunnel strap 2120. The length of the tunnel strap 2120 may be adjustable. The length of the tunnel strap 2120 may be adjusted through employment of a hook and loop fastener.

Figure 22A:
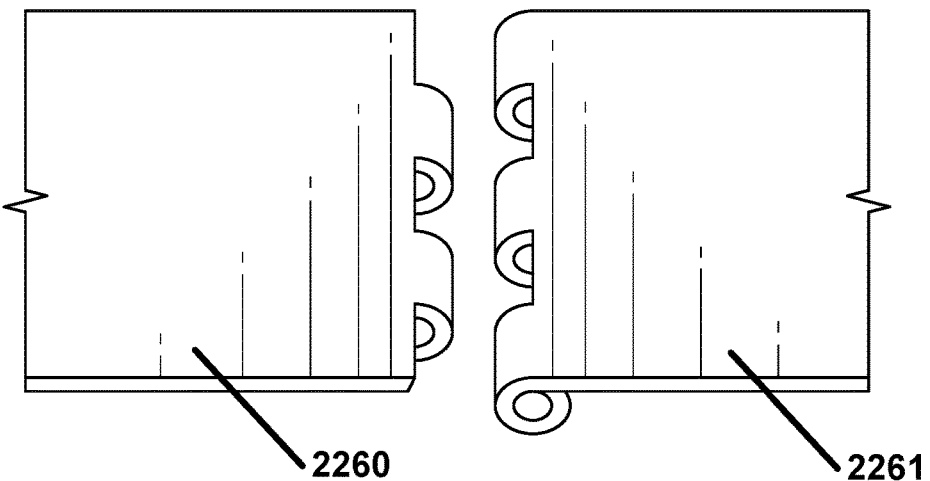
FIGS. 22A, 22B, and 22C illustrate a plurality of base plates and hinge components according to various aspects of various embodiments.
Figure 22B:
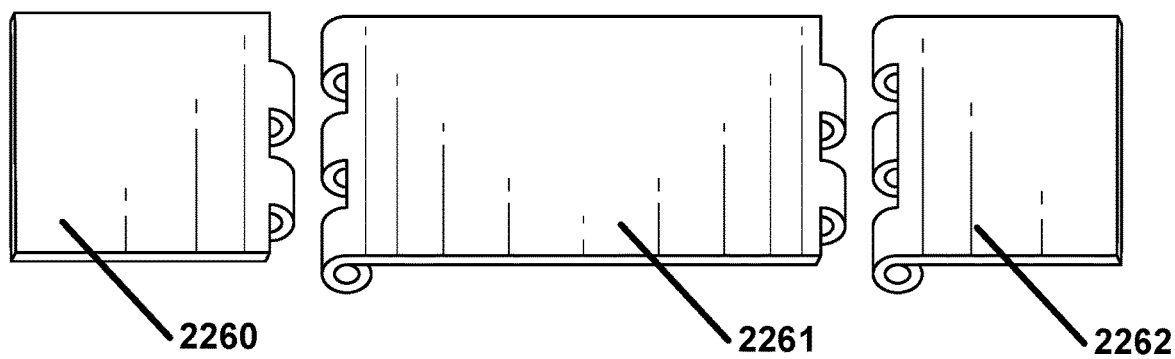
Figure 22C:
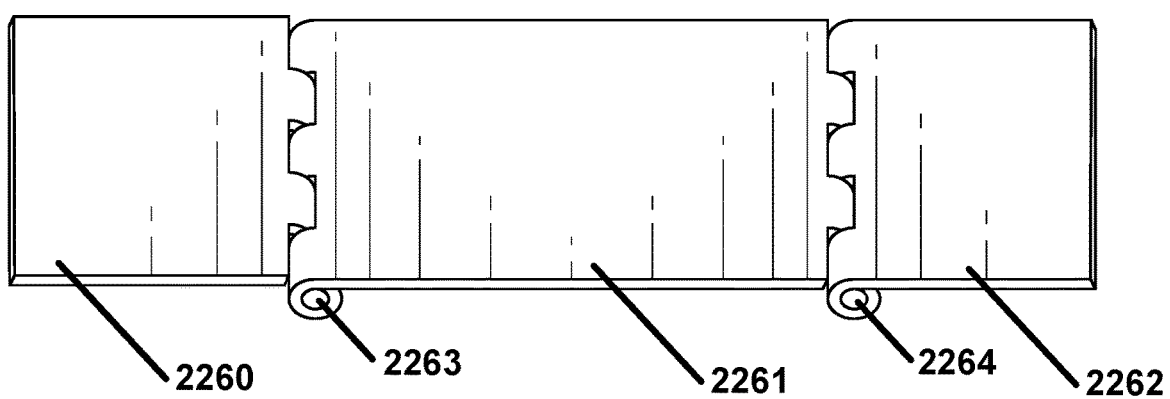

FIGS. 22A, 22B, and 22C illustrate a plurality of base plates (2260, 2261, and 2262) and hinge components according to various aspects of various embodiments. Hinge components may be integrated into each of the plurality of base plates (2260, 2261, and 2262). The plurality of base plates (2260, 2261, and 2262) may be connected through employment of at least one hinge pin (2263 and 2264).

Figure 23A:
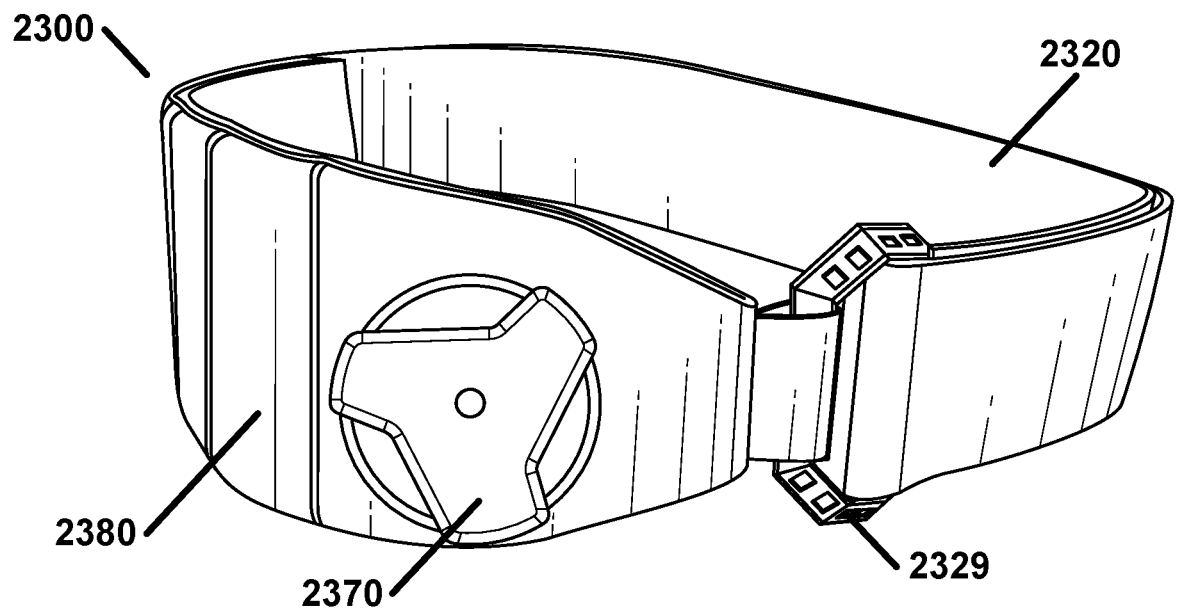
FIG. 23A illustrates an example tourniquet with a plurality of base plates and an outer cuff in an open position according to an aspect of an embodiment.

FIG. 23A illustrates an example tourniquet 2300 with a plurality of base plates and an outer cuff 2380 in an open position according to an aspect of an embodiment. The tourniquet 2300 may comprise a tightening mechanism 2370. The tourniquet 2300 may comprise a tunnel strap 2320. A first end of the tunnel strap 2320 may be connected to the tightening mechanism 2370 through employment of two laces. A second end of the tunnel strap 2320 may be connected to a tunnel strap loop connector 2329. The length of the tunnel strap 2320 may be adjustable. The length of the tunnel strap 2320 may be adjusted through employment of a hook and loop fastener.

Figure 23B:
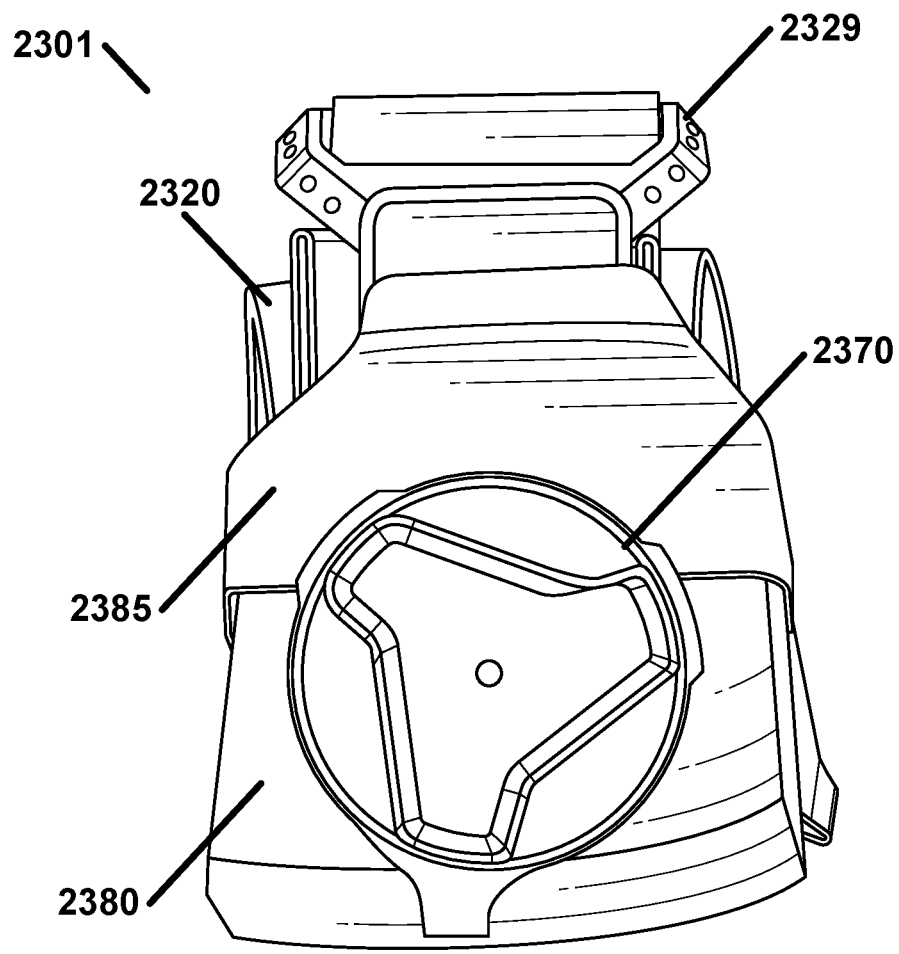
FIG. 23B illustrates an example tourniquet with a plurality of base plates and an outer cuff in a folded position according to an aspect of an embodiment.

FIG. 23B illustrates an example tourniquet 2301 with a plurality of base plates and an outer cuff 2380 in a folded position according to an aspect of an embodiment. The tourniquet 2301 may comprise a tightening mechanism 2370. The tourniquet 2301 may comprise a tunnel strap 2320. A first end of the tunnel strap 2320 may be connected to the tightening mechanism 2370 through employment of two laces. A second end of the tunnel strap 2320 may be connected to a tunnel strap loop connector 2329. The length of the tunnel strap 2320 may be adjustable. The length of the tunnel strap 2320 may be adjusted through employment of a hook and loop fastener. An elastic band 2385 may be employed to wrap around the tourniquet 2301 to maintain the folded position until the elastic band 2385 is removed.

Figure 24:
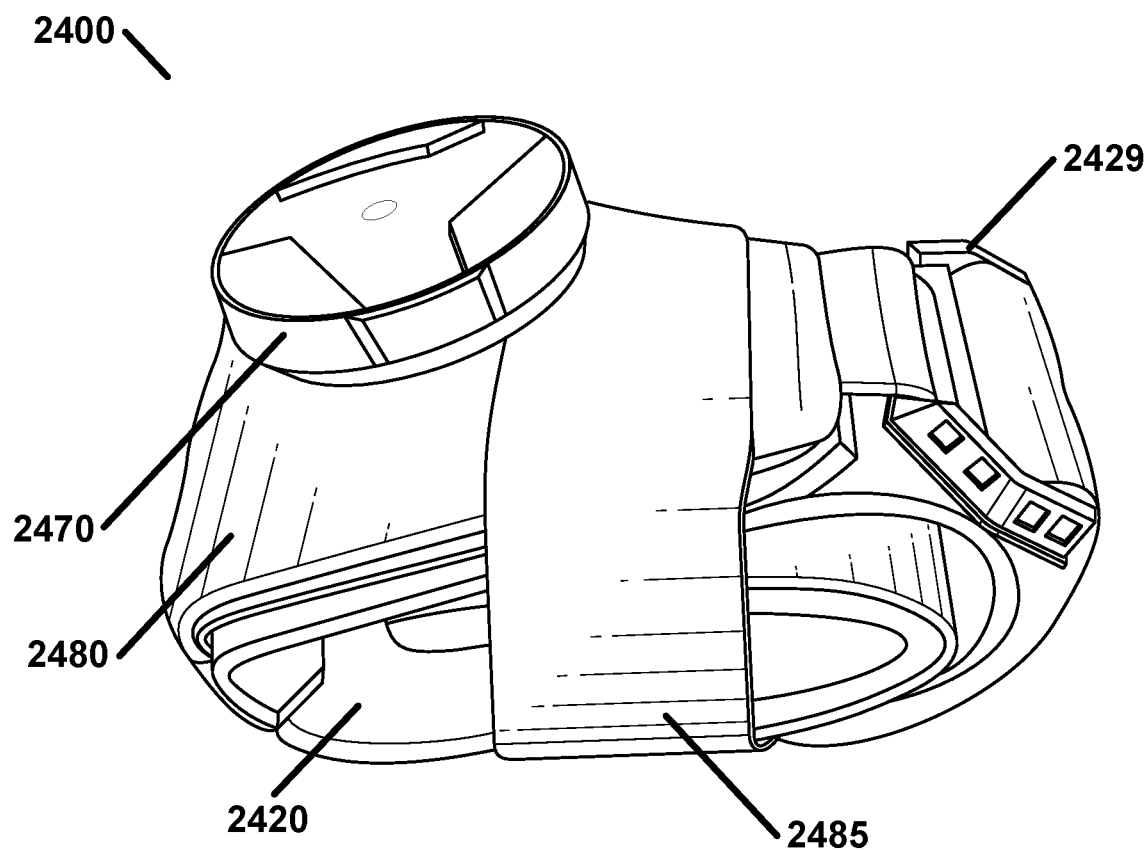
FIG. 24 illustrates an example tourniquet with a plurality of base plates and an outer cuff in a folded position according to an aspect of an embodiment.

FIG. 24 illustrates an example tourniquet 2400 with a plurality of base plates and an outer cuff 2480 in a folded position according to an aspect of an embodiment. The tourniquet 2400 may comprise a tightening mechanism 2470. The tourniquet 2400 may comprise a tunnel strap 2420. A first end of the tunnel strap 2420 may be connected to the tightening mechanism 2470 through employment of two laces. A second end of the tunnel strap 2420 may be connected to a tunnel strap loop connector 2429. The length of the tunnel strap 2420 may be adjustable. The length of the tunnel strap 2420 may be adjusted through employment of a hook and loop fastener. An elastic band 2485 may be employed to wrap around the tourniquet 2400 to maintain the folded position until the elastic band 2485 is removed.

Figure 25B:
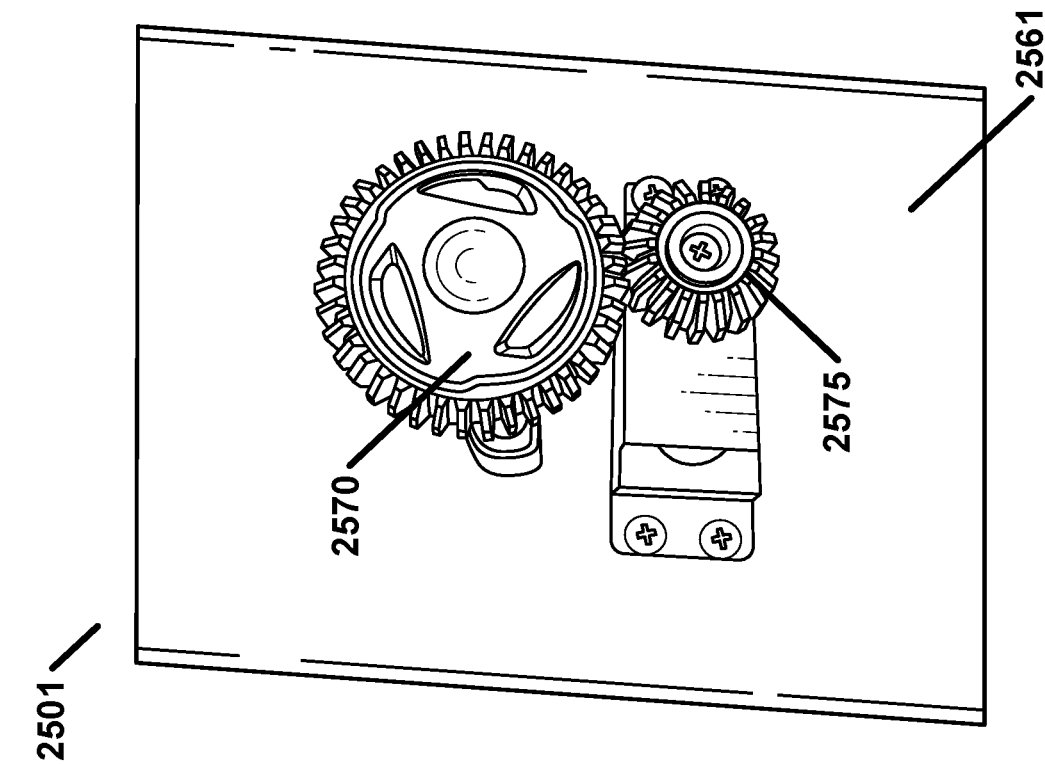
FIG. 25B illustrates an example electronic actuator and an example tightening mechanism connected to an example base plate of a portion of an example tourniquet according to an aspect of various embodiments.
Figure 25A:
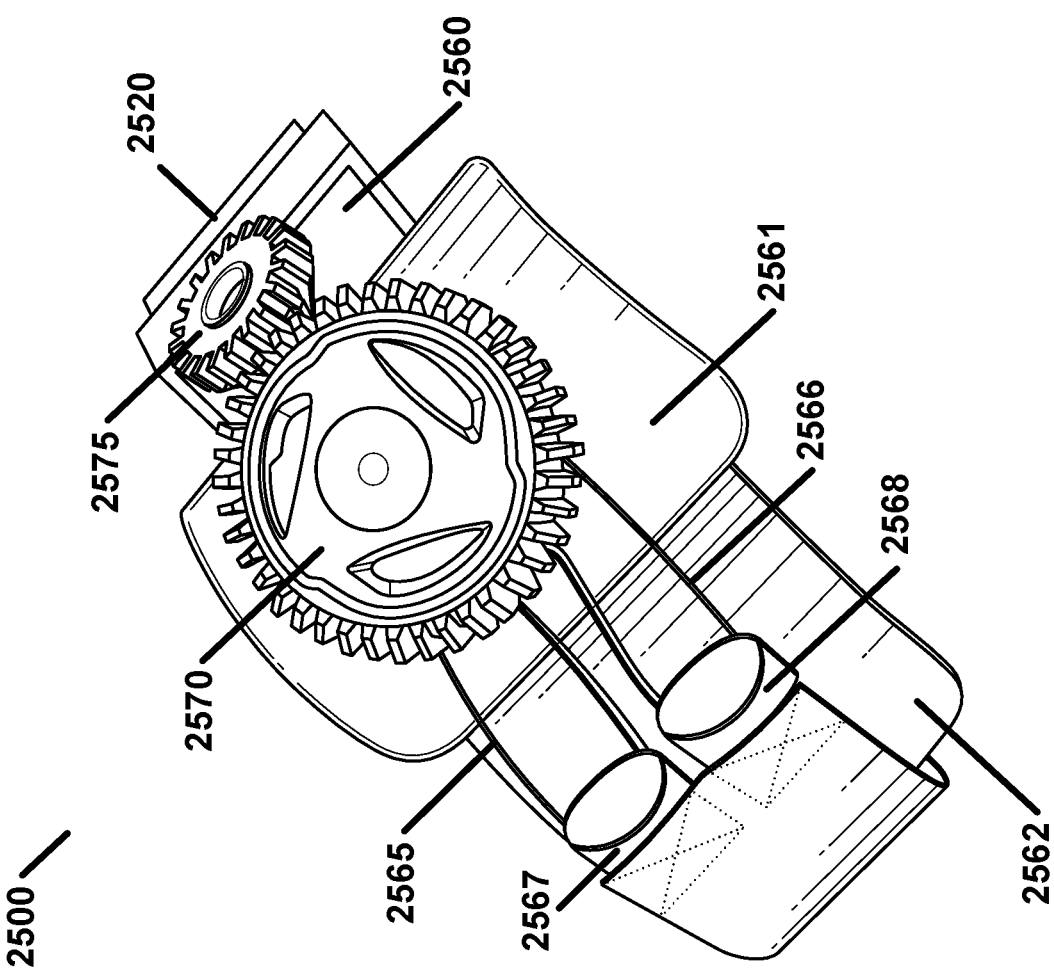
FIG. 25A illustrates an example electronic actuator and an example tightening mechanism of an example tourniquet according to an aspect of various embodiments.

FIG. 25A illustrates an example electronic actuator 2575 and an example tightening mechanism 2570 of an example tourniquet 2500 according to an aspect of various embodiments. The tourniquet 2500 may comprise at least one base plate (2560, 2561, and 2562). The tourniquet 2500 may comprise two laces (2565 and 2566). The tourniquet 2500 may comprise a tunnel strap 2520. The tunnel strap 2520 may comprise two lace guides (2567 and 2568) connected to a first end of the tunnel strap 2520. The tightening mechanism 2570 may be configured to be activated by the electronic actuator 2575.

FIG. 25B illustrates an example electronic actuator 2575 and an example tightening mechanism 2570 connected to an example base plate 2561 of a portion of an example tourniquet 2501 according to an aspect of various embodiments.

According to an embodiment, a tightening mechanism may require a tool to disengage or loosen a portion of two laces wound on a spool.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

In this specification, "a" and "an" and similar phrases are to be interpreted as "at least one" and "one or more." References to "a", "an", and "one" are not to be interpreted as "only one". In this specification, the term "may" is to be interpreted as "may, for example." In other words, the term "may" is indicative that the phrase following the term "may" is an example of one of a multitude of suitable possibilities that may, or may not, be employed to one or more of the various embodiments. In this specification, the phrase "based on" is indicative that the phrase following the term "based on" is an example of one of a multitude of suitable possibilities that may, or may not, be employed to one or more of the various embodiments. References to "an" embodiment in this disclosure are not necessarily to the same embodiment.

While various embodiments have been described above, it should be understood that they have been presented by way of example, and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. Thus, the present embodiments should not be limited by any of the above described exemplary embodiments.

In this specification, various embodiments are disclosed. Limitations, features, and/or elements from the disclosed example embodiments may be combined to create further embodiments within the scope of the disclosure.

In addition, it should be understood that any figures that highlight any functionality and/or advantages, are presented for example purposes only. The disclosed architecture is sufficiently flexible and configurable, such that it may be utilized in ways other than that shown. For example, the steps listed in any flowchart may be re-ordered or only optionally used in some embodiments.

Furthermore, many features presented above are described as being optional through the use of "may" or the use of parentheses. For the sake of brevity and legibility, the present disclosure does not explicitly recite each and every permutation that may be obtained by choosing from the set of optional features. However, the present disclosure is to be interpreted as explicitly disclosing all such permutations. For example, a system described as having three optional features may be embodied in seven different ways, namely with just one of the three possible features, with any two of the three possible features or with all three of the three possible features.

Further, the purpose of the Abstract of the Disclosure is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract of the Disclosure is not intended to be limiting as to the scope in any way.

Finally, it is the applicant's intent that only claims that include the express language "means for" or "step for" be interpreted under 35 U.S.C. 112. Claims that do not expressly include the phrase "means for" or "step for" are not to be interpreted under 35 U.S.C. 112.

What is claimed is:

1. A wearable device comprising:
   a) a tourniquet configured to occlude blood flow in an artery of a wearer, the tourniquet comprising:
      i) at least one base plate;
      ii) two anchor points, each of the two anchor points configured to anchor a first end of one of two laces to one of the at least one base plate;
      iii) a tunnel strap comprising two lace guides connected to a first end of the tunnel strap, each of the two lace guides configured to support lace travel, each of the two lace guides configured to guide one of the two laces; and
      iv) a tightening mechanism connected to one of the at least one base plate, the tightening mechanism comprising:
         A) a spool configured to accept a second end of each of the two laces; and
         B) a knob configured for manually winding a portion of the two laces onto the spool;
      v) wherein each of the two lace guides: is configured to receive one of the two laces from one of the two anchor points and is configured to guide one of the two laces directly to the spool, the two lace guides adjacent to each other on the first end of the tunnel strap; and
   b) a wearable item quick release connector connected to the tourniquet and configured to removably connect to a wearable item.

2. The wearable device according to claim 1, wherein the wearable item comprises at least one of the following:
   a) a ballistic plate carrier;
   b) a backpack;
   c) a belt; and
   d) a harness.

3. The wearable device according to claim 1, further comprising an outer cuff configured to cover at least a portion of the tourniquet.

4. The wearable device according to claim 1, wherein the tightening mechanism further comprises a housing configured to house:
   a) at least a portion of the spool; and
   b) the portion of the two laces.

5. The wearable device according to claim 4, wherein the housing is part of one of the at least one base plate.

6. The wearable device according to claim 1, wherein a first of the at least one base plate is connected to a second of the at least one base plate through employment of a first hinge.

7. The wearable device according to claim 6, wherein the second of the at least one base plate is connected to a third of the at least one base plate through employment of a second hinge.

8. The wearable device according to claim 1, wherein one of the at least one base plate is configured to receive a second end of the tunnel strap.

9. The wearable device according to claim 1, the tourniquet further comprising a tunnel strap quick release connector connected to one of the at least one base plate, the tunnel strap quick release connector configured to removably connect to a second end of the tunnel strap.

10. The wearable device according to claim 1, the tourniquet further comprising a tunnel strap loop connector connected to one of the at least one base plate, the tunnel strap loop connector configured to receive a second end of the tunnel strap.

11. A tourniquet configured to occlude blood flow in an artery of a wearer, the tourniquet comprising:
    a) at least one base plate;
    b) two anchor points, each of the two anchor points configured to anchor a first end of one of two laces to one of the at least one base plate;
    c) a tunnel strap comprising two lace guides connected to a first end of the tunnel strap, each of the two lace guides configured to support lace travel, each of the two lace guides configured to guide one of the two laces; and
    d) a tightening mechanism connected to one of the at least one base plate, the tightening mechanism comprising:
       i) a spool configured to accept a second end of each of the two laces; and
       ii) a knob configured for manually winding a portion of the two laces onto the spool;
    e) wherein each of the two lace guides: is configured to receive one of the two laces from one of the two anchor points and is configured to guide one of the two laces directly to the spools, the two lace guides adjacent to each other on the first end of the tunnel strap.

12. The tourniquet according to claim 11, further comprising an outer cuff configured to cover at least a portion of the at least one base plate.

13. The tourniquet according to claim 11, wherein the tightening mechanism further comprises a housing configured to house:
    a) at least a portion of the spool; and
    b) the portion of the two laces.

14. The tourniquet according to claim 13, wherein the housing is part of one of the at least one base plate.

15. The tourniquet according to claim 11, wherein a first of the at least one base plate is connected to a second of the at least one base plate through employment of a first hinge.

16. The tourniquet according to claim 15, wherein the second of the at least one base plate is connected to a third of the at least one base plate through employment of a second hinge.

17. The tourniquet according to claim 11, wherein one of the at least one base plate is configured to receive a second end of the tunnel strap.

18. The tourniquet according to claim 11, the tourniquet further comprising a tunnel strap quick release connector connected to one of the at least one base plate, the tunnel strap quick release connector configured to removably connect to a second end of the tunnel strap.

19. The tourniquet according to claim 11, the tourniquet further comprising a tunnel strap loop connector connected to one of the at least one base plate, the tunnel strap loop connector configured to receive a second end of the tunnel strap.

20. The tourniquet according to claim 11, wherein one of the at least one base plate comprises a tunnel strap loop connector configured to removably connect to a second end of the tunnel strap.

* * * * *